United States Patent
Ogino et al.

(10) Patent No.: US 9,073,376 B2
(45) Date of Patent: Jul. 7, 2015

(54) PHENOLSULFONIC ACID ARYL ESTER, DEVELOPING AGENT, AND HEAT-SENSITIVE RECORDING MATERIAL

(71) Applicants: NIPPON PAPER INDUSTRIES CO., LTD., Kita-ku (JP); MITSUBISHI CHEMICAL CORPORATION, Chiyoda-ku (JP)

(72) Inventors: Akihito Ogino, Tokyo (JP); Yoshimi Midorikawa, Tokyo (JP); Yukiko Sato, Tokyo (JP); Keiichiro Inada, Chikujo-gun (JP); Mai Higuchi, Chikujo-gun (JP); Mamoru Suga, Chiyoda-ku (JP)

(73) Assignees: NIPPON PAPER INDUSTRIES CO., LTD., Kita-ku, Tokyo (JP); Mitsubishi Chemical Corporation, Chiyoda-ku, Tokyo (JP)

( * ) Notice: Subject to any disclaimer, the term of this patent is extended or adjusted under 35 U.S.C. 154(b) by 0 days.

(21) Appl. No.: 14/355,118

(22) PCT Filed: Oct. 31, 2012

(86) PCT No.: PCT/JP2012/078096
§ 371 (c)(1),
(2) Date: Apr. 29, 2014

(87) PCT Pub. No.: WO2013/065704
PCT Pub. Date: May 10, 2013

(65) Prior Publication Data
US 2014/0315713 A1    Oct. 23, 2014

(30) Foreign Application Priority Data
Oct. 31, 2011 (JP) ................. 2011-239763

(51) Int. Cl.
| | | |
|---|---|---|
| *B41M 5/333* | (2006.01) | |
| *B41M 5/337* | (2006.01) | |
| *C07C 309/75* | (2006.01) | |
| *C07C 309/77* | (2006.01) | |

(52) U.S. Cl.
CPC ............ *B41M 5/3336* (2013.01); *C07C 309/75* (2013.01); *C07C 309/77* (2013.01); *B41M 5/3375* (2013.01)

(58) Field of Classification Search
CPC .. B41M 5/3336; B41M 5/3375; B41M 5/333; B41M 5/337; C07C 309/77; C07C 309/75

USPC .............................. 503/209, 216; 558/52, 58
See application file for complete search history.

(56) References Cited

U.S. PATENT DOCUMENTS

| | | |
|---|---|---|
| 4,583,104 A | 4/1986 | Iwakura et al. |
| 2013/0237414 A1 | 9/2013 | Higuchi et al. |

FOREIGN PATENT DOCUMENTS

| | | |
|---|---|---|
| JP | 60-054884 A | 3/1985 |
| JP | 60-176794 A | 9/1985 |
| JP | 2010-053128 A | 3/2010 |
| WO | WO 96/08483 A1 | 3/1996 |
| WO | WO 2012/036267 A1 | 3/2012 |

OTHER PUBLICATIONS

International Search Report issued Jan. 29, 2013 in PCT/JP2012/078096.

*Primary Examiner* — Bruce H Hess
(74) *Attorney, Agent, or Firm* — Oblon, McClelland, Maier & Neustadt, L.L.P.

(57) ABSTRACT

The present invention provides a compound represented by the formula (1). The compound represented by the formula (1) is a developing agent superior in both color-developing sensitivity with low energy and image stability [in the following formula, wherein $R^1$ is a hydrogen atom, an alkyl group, an alkenyl group, an aryl group or an aralkyl group, $R^2$ in the number of m are each independently an alkyl group, an alkenyl group, an aryl group, an aralkyl group, an alkoxy group, a halogen atom, a hydroxy group, a cyano group, a nitro group, a carboxy group or an amino group, $R^3$ in the number of n are each independently an alkyl group, an alkenyl group, an aryl group, an aralkyl group, an alkoxy group, a halogen atom, a hydroxy group, a cyano group, a nitro group, a carboxy group or an amino group, and m and n are each independently an integer of 0-4.

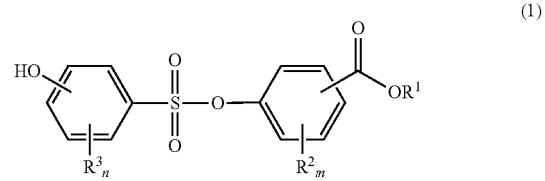

(1)

20 Claims, No Drawings

PHENOLSULFONIC ACID ARYL ESTER, DEVELOPING AGENT, AND HEAT-SENSITIVE RECORDING MATERIAL

TECHNICAL FIELD

The present invention relates to a phenolsulfonic acid aryl ester useful as a developer. Furthermore, the present invention also relates to a developer and a thermal recording material, which contain the aforementioned phenolsulfonic acid aryl ester.

BACKGROUND ART

Generally, thermal recording materials having a thermal recording layer based mainly on a colorless or pale-colored basic (electron-donating) leuco dye (hereinafter sometimes to be abbreviated as "dye") and an electron-accepting developer that develops color by reacting with dye on heating (hereinafter sometimes to be abbreviated as "developer") are widely used in practice. For recording on the thermal recording materials, a thermal printer with a built-in thermal head, and the like are used. This method of thermal recording is advantageous over other conventional recording methods in practical use, with features such as (a) noiselessness during recording, (b) obviation of the need for development and fixation, (c) freedom from maintenance work, (d) relatively inexpensive instrumentation, (e) compactness, and (f) very vivid colors developing in the images obtained, and is widely used for facsimiles, computer terminal printers, automated ticket machines, measurement recorders, handy terminals for outdoor use, and the like. In recent years, to reduce consumption power by down-sizing these instruments, a material showing high color-developing sensitivity even with low energy, free of background fog (unintended color development on a white blank area due to heating during storage and the like), and showing superior image stability is required.

A factor having a great influence on the color-developing sensitivity is selection of the dye and developer (particularly developer) constituting the thermal recording layer. Various developers have been studied heretofore. For example, benzyl p-hydroxybenzoate expected at one time as a high sensitive developer is no longer used at present, since image stability is markedly low. In addition, bisphenol A (that is, 4,4'-isopropylidenediphenol) shows insufficient color-developing sensitivity and unsatisfactory image stability such as plasticizer resistance and heat resistance. Furthermore, since bisphenol A is suspected to have an environment hormone activity, the world's strong tendency is to ban the use thereof. In fact, some countries have banned the use of a thermal recording material using bisphenol A. To solve this problem, bisphenol S (i.e., 4,4'-dihydroxydiphenylsulfone) is sometimes used as a developer. However, bisphenol S is disadvantageous in that it has high melting point and low color-developing sensitivity.

In addition, patent document 1 describes use of a phenol derivative containing an aryloxysulfonyl group optionally having substituent(s) as an electron accepting compound (developer), and recites a chlorine atom, an alkyl group and the like as the substituent of the aryl group. However, patent document 1 does not describe an alkoxycarbonyl group and a carboxy group as the substituent of the aryl group. While the aryloxysulfonyl group-containing phenol derivative described in patent document 1, which has a chlorine atom or an alkyl group as the substituent of the aryl group, shows good color-developing sensitivity but defectively shows inferior background fog and unclear contrast between blank area and recorded area.

DOCUMENT LIST

Patent Document patent document 1: JP-A-S60-54884

SUMMARY OF THE INVENTION

Problems to be Solved by the Invention

For downsizing of instrument and the like in recent years, a thermal recording material (particularly a developer constituting same) is required to show good color development even with low energy (that is, good color-developing sensitivity even with low energy). However, a developer showing high color-developing sensitivity with low energy is inferior in the background fog and image stability (heat resistance, resistance to plasticizer etc.) On the other hand, when background fog and image stability of a developer are to be improved, problems occur that the molecular weight of the developer increases and the melting point thereof increases, and the color-developing sensitivity with low energy decreases. Therefore, a developer superior in the balance of color-developing sensitivity with low energy, background fog and image stability (heat resistance, resistance to plasticizer etc.) does not exist to date.

The present invention has been made taking note of the above-mentioned situation and aims to provide a developer superior in the balance of color-developing sensitivity with low energy, background fog and image stability.

Means of Solving the Problems

The present inventors have conducted intensive studies and found that a phenolsulfonic acid aryl ester having a particular structure represented by the formula (1) is a developer superior in the balance of color-developing sensitivity with low energy, background fog and image stability. The present invention based on this finding is as described below.

[1] A compound represented by the formula (1)

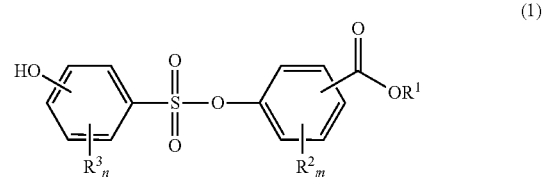

wherein $R^1$ is a hydrogen atom, an alkyl group, an alkenyl group, an aryl group or an aralkyl group, $R^2$ in the number of m are each independently an alkyl group, an alkenyl group, an aryl group, an aralkyl group, an alkoxy group, a halogen atom, a hydroxy group, a cyano group, a nitro group, a carboxy group or an amino group, $R^3$ in the number of n are each independently an alkyl group, an alkenyl group, an aryl group, an aralkyl group, an alkoxy group, a halogen atom, a hydroxy group, a cyano group, a nitro group, a carboxy group or an amino group, and m and n are each independently an integer of 0-4.

[2] The compound of the above-mentioned [1], wherein the —CO—OR$^1$ group is bound to a carbon atom at the 2-position or 4-position of a benzene ring. [3] A developer for a thermal recording material, comprising the compound of the above-mentioned [1] or [2].
[4] A thermal recording material comprising a support, and a thermal recording layer provided on the support,
wherein the thermal recording layer comprises a colorless or pale-colored basic leuco dye and a developer for color development of the basic leuco dye, and
the developer comprises the compound of the above-mentioned [1] or [2].
[5] The thermal recording material of the above-mentioned [4], wherein the thermal recording layer comprises a second developer different from the compound of the above-mentioned [1] or [2].
[6] The thermal recording material of the above-mentioned [5], wherein the second developer is at least one selected from the group consisting of a bisphenol sulfone compound, a bisphenol compound, a urea compound and a novolac type phenol compound. [7] The thermal recording material of any one of the above-mentioned [4] to [6], wherein the thermal recording layer comprises at least one sensitizer selected from the group consisting of 1,2-di-(3-methylphenoxy) ethane, fatty acid amide having 10 to 21 carbon atoms, β-benzyloxynaphthalene, diphenylsulfone and p-toluenesulfonamide.
[8] The thermal recording material of any one of the above-mentioned [4] to [7], wherein the thermal recording layer comprises a hindered phenol compound.
[9] The thermal recording material of the above-mentioned [8], wherein the hindered phenol compound is at least one selected from the group consisting of a compound represented by the formula (2), a compound represented by the formula (3) and a compound represented by the formula (4):

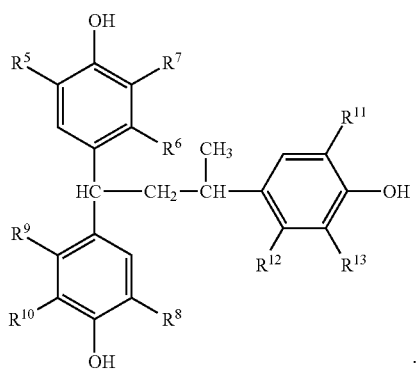

(2)

wherein R$^5$, R$^8$ and R$^{11}$ are each independently an alkyl group, and R$^6$, R$^7$, R$^9$, R$^{10}$, R$^{12}$ and R$^{13}$ are each independently a hydrogen atom or an alkyl group,

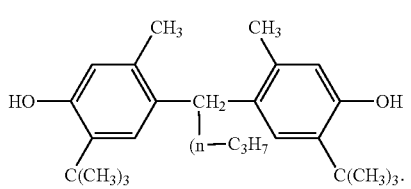

(3)

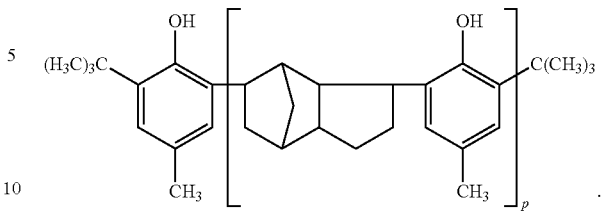

(4)

wherein p is 1 or 2.
[10] The thermal recording material of the above-mentioned [9], wherein R$^5$, R$^8$ and R$^{11}$ are tert-butyl groups or cyclohexyl groups, R$^6$, R$^9$ and R$^{12}$ are methyl groups, and R$^7$, R$^{10}$ and R$^{13}$ are hydrogen atoms.

Hereinafter the "compound represented by the formula (1)" is sometimes abbreviated as "compound (1)". Also, the compounds represented by other formulas are sometimes abbreviated in the same manner.

Effect of the Invention

Using the compound (1) of the present invention (phenolsulfonic acid aryl ester) as a developer, a thermal recording material superior in the balance of the color-developing sensitivity with low energy, background fog and image stability (heat resistance, resistance to plasticizer etc.) can be obtained.

DESCRIPTION OF EMBODIMENTS

<Compound (1)>

First, the compound (1) of the present invention is explained. R$^1$ in the formula (1) is a hydrogen atom, an alkyl group, an alkenyl group, an aryl group or an aralkyl group.

The carbon number of the alkyl group for R$^1$ is preferably 1-8, more preferably 1-6, further preferably 1-4. The alkyl group for R$^1$ may be linear, branched chain or cyclic. The alkyl group for R$^1$ is preferably linear or branched chain. Examples of the alkyl group include a methyl group, an ethyl group, a propyl group, an isopropyl group, a butyl group, an isobutyl group, a sec-butyl group, a tert-butyl group, a pentyl group, an isopentyl group, a sec-pentyl group, a tert-pentyl group, a 2-methylbutyl group, a hexyl group, an isohexyl group, a sec-hexyl group, a tert-hexyl group, a cyclohexyl group, a heptyl group, an octyl group, an isooctyl group, a sec-octyl group, a tert-octyl group, a 2-ethylhexyl group and the like.

The carbon number of the alkenyl group for R$^1$ is preferably 2-8, more preferably 2-6, further preferably 2-4. The alkenyl group for R$^1$ may be linear, branched chain or cyclic. The alkenyl group for R$^1$ is preferably linear or branched chain. Examples of the alkenyl group include a vinyl group, an allyl group, an isopropenyl group, a 1-propenyl group, a 2-butenyl group, a 3-butenyl group, a 1,3-butanedienyl group, a 2-methyl-2-propenyl group and the like. Among these, a vinyl group and an allyl group are preferable.

The aryl group may be a monocycle or fused ring. The carbon number of the aryl group for R$^1$ is preferably 6-14, more preferably 6-10. Examples of the aryl group include a phenyl group, a naphthyl group, an anthryl group, a phenanthryl group and the like. Among these, a phenyl group is preferable. In addition, the aryl group may have one or more substituent(s). Examples of the substituent of the aryl group include an alkyl group, an aryl group, a hydroxy group, a halogen atom, a nitro group, a carboxy group, an amino group and the like.

The carbon number of the aralkyl group for $R^1$ is preferably 7-15, more preferably 7-8. Examples of the aralkyl group include a phenylmethyl group (benzyl group), a phenylethyl group (phenethyl group), a diphenylmethyl group, a 3-phenylpropyl group, a 2-phenylpropyl group, a 4-phenylbutyl group, a biphenylmethyl group, a naphthylmethyl group and the like. Among these, a benzyl group and a phenethyl group are preferable.

$R^2$ and $R^3$ in the formula (1) are each independently an alkyl group, an alkenyl group, an aryl group, an aralkyl group, an alkoxy group, a halogen atom, a hydroxy group, a cyano group, a nitro group, a carboxy group or an amino group. Explanations of the alkyl group, alkenyl group, aryl group and aralkyl group for $R^2$ or $R^3$ are the same as the above.

The carbon number of the alkoxy group for $R^2$ or $R^3$ is preferably 1-8, more preferably 1-4. The alkoxy group may be linear or branched chain. Examples of the alkoxy group include a methoxy group, an ethoxy group, a propoxy group, an isopropoxy group, a butoxy group, an isobutoxy group, a tert-butoxy group, a pentoxy group, an isopentoxy group, a neopentoxy group, a tert-pentoxy group, a hexyloxy group, an isohexyloxy group and the like. Among these, a methoxy group, an ethoxy group, a propoxy group, an isopropoxy group and a tert-butoxy group are preferable.

Examples of the halogen atom include a chlorine atom, a bromine atom, a fluorine atom and an iodine atom. Among these, a chlorine atom and a bromine atom are preferable.

In the formula (1), m and n are each independently an integer of 0-4. When m and n are 0, it means $R^2$ and $R^3$ are respectively absent. In addition, when m is two or more, $R^2$ in the number of m may be the same as or different from each other. Similarly, when n is two or more, $R^3$ in the number of n may be the same as or different from each other. m is preferably 0 or 1, more preferably O. n is preferably an integer of 0-2, more preferably 0 or 1, further preferably O.

As the combination of $R^1$-$R^3$, m and n,
a combination wherein
$R^1$ is a hydrogen atom, an alkyl group having a carbon number of 1-6 or an aralkyl group having a carbon number of 7-8,
$R^2$ in the number of m are each independently an alkyl group having a carbon number of 1-6, an alkoxy group having a carbon number of 1-4 or a carboxy group,
$R^3$ in the number of n are each independently an alkyl group having a carbon number of 1-6, an alkoxy group having a carbon number of 1-4 or a carboxy group, and
m and n are each independently an integer of 0-2 is preferable;
a combination wherein
$R^1$ is a hydrogen atom, an alkyl group having a carbon number of 1-6 or an aralkyl group having a carbon number of 7-8,
$R^2$ is an alkyl group having a carbon number of 1-6, an alkoxy group having a carbon number of 1-4 or a carboxy group,
$R^3$ in the number of n are each independently an alkyl group having a carbon number of 1-6, an alkoxy group having a carbon number of 1-4 or a carboxy group,
m is 0 or 1, and
n is an integer of 0-2 is more preferable; a combination wherein
$R^1$ is an alkyl group having a carbon number of 1-6,
$R^2$ is an alkyl group having a carbon number of 1-6,
$R^3$ is an alkyl group having a carbon number of 1-6 or a carboxy group, and
m and n are each independently 0 or 1
is further preferable; and
a combination wherein
$R^1$ is an alkyl group having a carbon number of 1-6, and
m and n are 0
is particularly preferable.

The position of the —CO—$OR^1$ group in the formula (1) is preferably the 2-position or the 4-position, more preferably the 2-position, when the carbon atom to which an oxy group (—O—) in the benzene ring having a —CO—$OR^1$ group is bonded is the 1-position. In the present invention, the position of $R^2$ in the formula (1) is not particularly limited.

The position of the —OH group in the formula (1) is preferably the 4-position when the carbon atom to which a sulfonyl group (—$SO_2$—) in the benzene ring having an —OH group is bonded is the 1-position. The position of $R^3$ is preferably the 3-position, or the 3-position and the 5-position.

Of the compounds (1) of the present invention, a compound wherein
$R^1$ is an alkyl group having a carbon number of 1-6,
$R^2$ is an alkyl group having a carbon number of 1-6,
$R^3$ in the number of n are each independently an alkyl group having a carbon number of 1-6 or a carboxy group,
m is an integer of 0 or 1,
n is an integer of 0-2,
the position of the —CO—$OR^1$ group is the 2-position or the 4-position when the carbon atom to which an oxy group (—O—) in the benzene ring having a —CO—$OR^1$ group is bonded is the 1-position, and
the position of the —OH group is the 4-position when the carbon atom to which a sulfonyl group (—$SO_2$—) in the benzene ring having an —OH group is bonded is the 1-position, is preferable; and
the compounds represented by the following formulas (a1)-(a26) are more preferable.

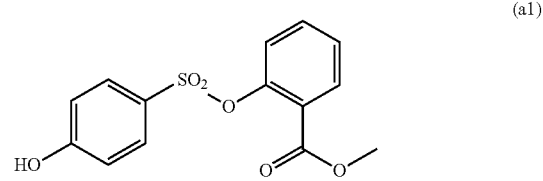

(a1)

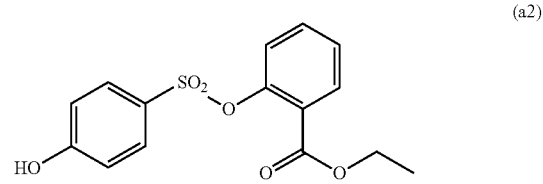

(a2)

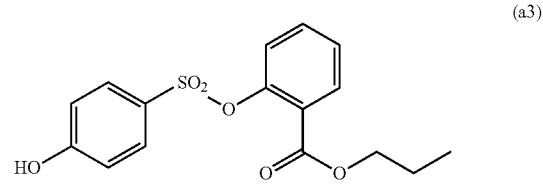

(a3)

(a4)
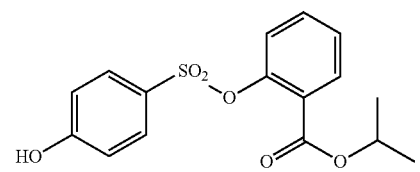
(a5)
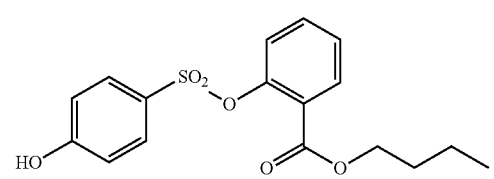
(a6)
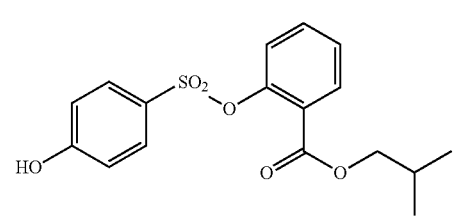
(a7)
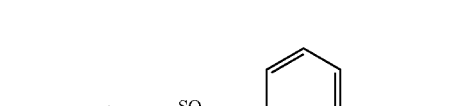
(a8)
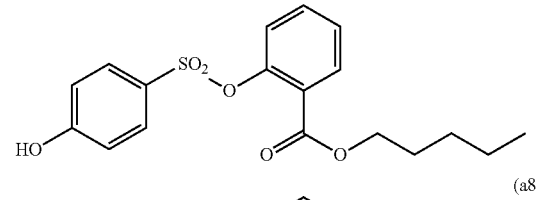
(a9)
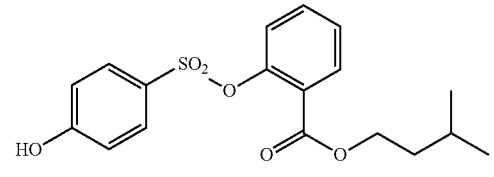
(a10)
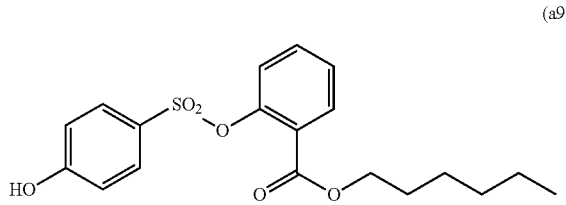
(a11)
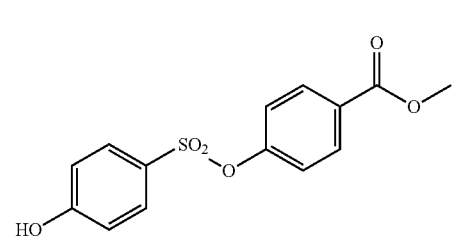
(a12)
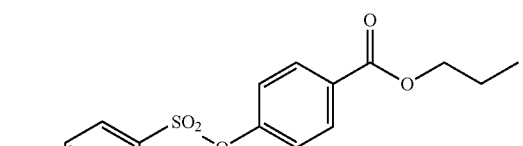
(a13)
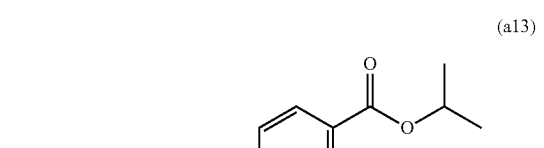
(a14)
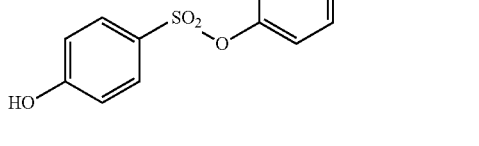
(a15)
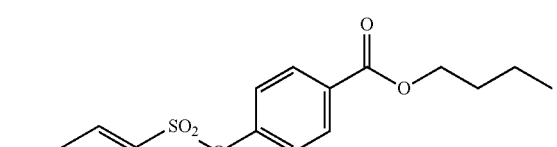
(a16)
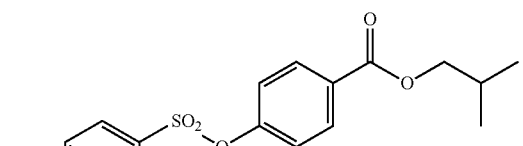
(a17)
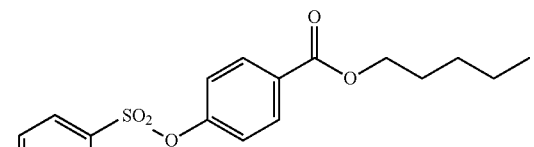

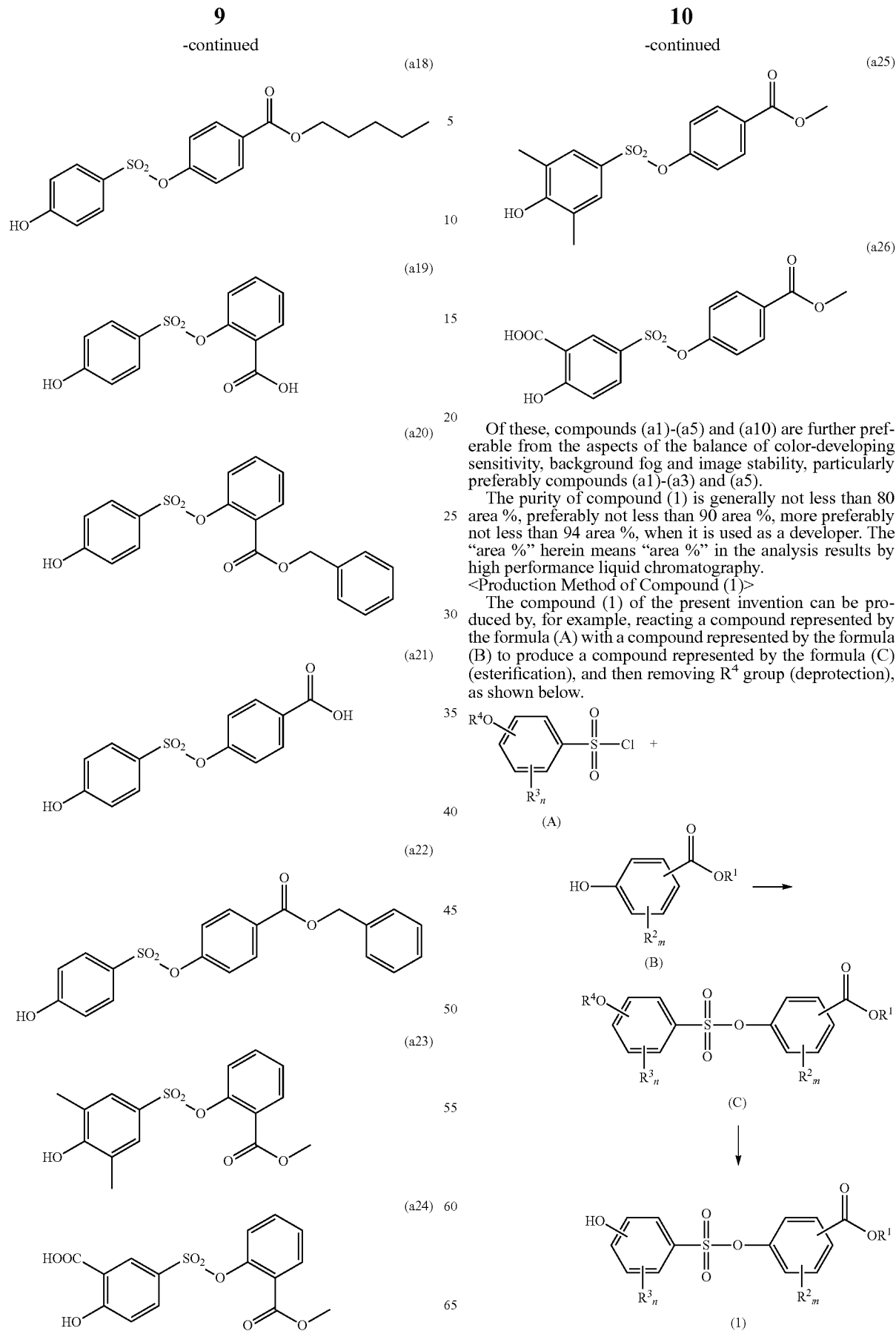

Of these, compounds (a1)-(a5) and (a10) are further preferable from the aspects of the balance of color-developing sensitivity, background fog and image stability, particularly preferably compounds (a1)-(a3) and (a5).

The purity of compound (1) is generally not less than 80 area %, preferably not less than 90 area %, more preferably not less than 94 area %, when it is used as a developer. The "area %" herein means "area %" in the analysis results by high performance liquid chromatography.

<Production Method of Compound (1)>

The compound (1) of the present invention can be produced by, for example, reacting a compound represented by the formula (A) with a compound represented by the formula (B) to produce a compound represented by the formula (C) (esterification), and then removing $R^4$ group (deprotection), as shown below.

Esterification of compound (A) and compound (B) can be performed according to a known method (e.g., the method described in JP-A-2010-53128). $R^4$ is a protecting group of a hydroxy group, and examples thereof include an acetyl group and the like. Deprotection of compound (C) can also be performed according to a known method.

<Developer for Thermal Recording Material>

The present invention also provides a developer for a thermal recording material containing compound (1) (hereinafter sometimes to be abbreviated as "the developer of the present invention"). Only one kind of compound (1) may be used or two or more kinds thereof may be used in combination. The developer of the present invention may contain a developer other than compound (1) (e.g., below-mentioned second developer). The content of compound (1) in the developer of the present invention is preferably not less than 50 wt %, more preferably not less than 60 wt %, further preferably not less than 70 wt %.

<Heat-Sensitive Recording Material>

The present invention also provides a thermal recording material having a support, and a thermal recording layer (heat-sensitive color development layer) provided on the support. In the thermal recording material of the present invention, the thermal recording layer contains a colorless or a pale-colored basic (electron-donating) leuco dye, and a developer for developing the color of the basic leuco dye, and the developer contains compound (1). In the thermal recording material of the present invention, only one kind of compounds (1) may be used, or two or more kinds thereof may be used in combination. The content of compound (1) in the thermal recording layer is generally 0.1-10 parts by weight, preferably 0.5-8 parts by weight, particularly preferably 1-5 parts by weight, relative to 1 part by weight of the basic leuco dye.

In the following, the components other than compound (1) (second developer, basic leuco dye, sensitizer, stabilizer, binder, crosslinking agent, pigment, lubricant, other additives) usable for forming a thermal recording layer are explained in this order. Only one kind of the component other than compound (1) may be used, or two or more kinds thereof may be used in combination. The binder, crosslinking agent, pigment and the like can be used for not only the thermal recording layer but also a layer other than the thermal recording layer (e.g., below-mentioned protection layer) that the thermal recording material of the present invention can have.

<Second Developer>

The thermal recording layer may contain a second developer different from the compound (1) of the present invention (preferably an electron accepting developer), as long as the effect of the present invention is not inhibited. As the second developer, any developer conventionally known in the field of pressure sensitive or thermal recording paper can be used, and is not particularly limited. Only one kind of the second developer may be used, or two or more kinds thereof may be used in combination. When the second developer is used, the amount thereof to be used is preferably 0.005-1 part by weight, more preferably 0.01 part by weight-0.8 part by weight, further preferably 0.02 part by weight-0.7 part by weight, relative to 1 part by weight of the compound (1).

Using the second developer, a superior thermal recording material maintaining high color-developing sensitivity, and showing further improved image stability such as heat resistance, moisture resistance and water resistance can be provided.

As the second developer in the present invention, preferred are a bisphenol sulfone compound, a bisphenol compound, a urea compound and a novolac type phenol compound. Specific examples of the representative developer are as follows.

<Bisphenol Sulfone Compound>

4,4'-dihydroxydiphenylsulfone, 2,4'-dihydroxydiphenylsulfone, 4-hydroxy-4'-propoxydiphenylsulfone, 4-hydroxy-4'-isopropoxydiphenylsulfone, 4-hydroxy-4'-allyloxydiphenylsulfone, bis(3-allyl-4-hydroxyphenyl)sulfone, 4-hydroxyphenyl-4'-benzyloxyphenylsulfone, 3,4-dihydroxyphenyl-4'-methylphenylsulfone, bisphenol sulfone crosslinking type compound described in JP-B-3913820, and bisphenol sulfone derivative described in JP-B-4004289

<Bisphenol Compound>

4,4'-isopropylidenediphenol, 2,2'-bis(4-hydroxy-3-methylphenyl)propane, 1,1-bis(4-hydroxyphenyl)cyclohexane, 2,2-bis(4-hydroxyphenyl)-4-methylpentane, 1,1-bis(4-hydroxyphenyl)-1-phenylethane described in JP-B-4216325, 4,4'-dihydroxydiphenylsulfide, di(4-hydroxy-3-methylphenyl)sulfide, 2,2'-thiobis(3-tert-octylphenol), and 2,2'-thiobis(4-tert-octylphenol)

<Urea Compound>

4,4'-bis(3-(phenoxycarbonylamino)methylphenylureido) diphenylsulfone, N-(p-toluenesulfonyl)-N'-(3-p-toluenesulfonyloxyphenyl)urea described in JP-B-4601174 and a derivative thereof, 4,4'-bis(p-toluenesulfonylaminocarbonylamino) diphenylmethane <Novolac Type Phenol Compound> phenol-formalin condensation product described in WO02/098674

<Others> inorganic acidic substances such as activated clay, attapulgite, colloidal silica, aluminum silicate, hydroquinone monobenzyl ether, benzyl 4-hydroxybenzoate, aminobenzenesulfonamide derivative described in JP-A-H08-59603, bis (4-hydroxyphenylthioethoxy)methane, 1,5-di(4-hydroxyphenylthio)-3-oxapentane, butyl bis(p-hydroxyphenyl)acetate, methyl bis(p-hydroxyphenyl)acetate, 1,1-bis(4-hydroxyphenyl)-1-phenylethane, 1,4-bis[α-methyl-α-(4'-hydroxyphenyl)ethyl]benzene, 1,3-bis[α-methyl-α-(4'-hydroxyphenyl)ethyl]benzene, the compound described in WO02/081229 or JP-A-2002-301873, thiourea compounds such as N,N'-di-m-chlorophenylthiourea, aromatic carboxylic acids such as p-chlorobenzoic acid, stearyl gallate, bis [zinc 4-(n-octyloxycarbonylamino) salicylate]dihydrate, 4-[2-(p-methoxyphenoxy)ethyloxy]salicylic acid, 4-[3-(p-tolylsulfonyl)propyloxy]salicylic acid, 5-[p-(2-p-methoxyphenoxyethoxy)cumyl]salicylic acid and salts of these aromatic carboxylic acid with a polyvalent metal salts such as zinc, magnesium, aluminum, calcium, titanium, manganese, tin, nickel; zinc thiocyanate antipyrine complex, composite zinc salt of terephthalaldehyde acid and other aromatic carboxylic acid, higher fatty acid metal double salt described in JP-A-H10-258577, metal chelate complex of polyvalent hydroxyaromatic compound and the like Among the aforementioned second developers, 4,4'-dihydroxydiphenylsulfone, 2,4'-dihydroxydiphenylsulfone, 4-hydroxy-4'-propoxydiphenylsulfone, 4-hydroxy-4'-isopropoxydiphenylsulfone, 4-hydroxy-4'-allyloxydiphenylsulfone, bis(3-allyl-4-hydroxyphenyl)sulfone, 4,4'-isopropylidenediphenol, 2,2'-bis(4-hydroxy-3-methylphenyl) propane, diphenylsulfone crosslinking compound described in JP-B-3913820, diphenylsulfone derivative described in JP-B-4004289, phenol-formalin condensate described in WO02/098674, 4,4'-bis(3-(phenoxycarbonylamino)methylphenylureido)diphenylsulfone, N-(p-toluenesulfonyl)-N'-(3-p-toluenesulfonyloxyphenyl)urea described in JP-B-4601174 and a derivative thereof are preferable, 4,4'-dihydroxydiphenylsulfone, 2,4'-dihydroxydiphenylsulfone, 4-hydroxy-4'- propoxydiphenylsulfone, 4-hydroxy-4'-isopropoxydiphenyl-sulfone, 4-hydroxy-4'-allyloxydiphenylsulfone, bis(3-allyl-4-hydroxyphenyl)sulfone, bisphenol sulfone crosslinking compound described in JP-B-3913820, and bisphenol sulfone derivative described in JP-B-4004289 are more preferable. When they are used, image stability (heat resistance, resistance to plasticizer, moisture resistance, water resistance) and the like of the thermal recording material can be improved while maintaining the color-developing sensitivity thereof.

<Basic Leuco Dye>

As the colorless or pale-colored basic (electron-donating) leuco dye, all of those conventionally known in the field of pressure sensitive or thermal recording paper can be used. Although it is not particularly limited, triphenylmethane leuco dye, fluoran leuco dye, fluorene leuco dye, divinyl leuco dye and the like are preferable. Specific examples of representative colorless or pale-colored dye (dye precursor) are shown below. Only one kind of these dyes (dye precursors) may be used or two or more kinds thereof may be used in combination.

<Triphenylmethane Leuco Dye>

3,3-bis(p-dimethylaminophenyl)-6-dimethylaminophthalide [other name, crystal violet lactone]; 3,3-bis(p-dimethylaminophenyl)phthalide [other name, malachite green lactone]

<Fluoran Leuco Dye>

3-diethylamino-6-methylfluoran; 3-diethylamino-6-methyl-7-anilinofluoran; 3-diethylamino-6-methyl-7-(o,p-dimethylanilino)fluoran; 3-diethylamino-6-methyl-7-chlorofluoran; 3-diethylamino-6-methyl-7-(m-trifluoromethylanilino)fluoran; 3-diethylamino-6-methyl-7-(o-chloroanilino)fluoran; 3-diethylamino-6-methyl-7-(p-chloroanilino)fluoran; 3-diethylamino-6-methyl-7-(o-fluoroanilino)fluoran; 3-diethylamino-6-methyl-7-(m-methylanilino)fluoran; 3-diethylamino-6-methyl-7-octylanilinofluoran; 3-diethylamino-6-methyl-7-octylaminofluoran; 3-diethylamino-6-methyl-7-benzylaminofluoran; 3-diethylamino-6-methyl-7-dibenzylaminofluoran;

3-diethylamino-6-chloro-7-methylfluoran; 3-diethylamino-6-chloro-7-anilinofluoran; 3-diethylamino-6-chloro-7-p-methylanilinofluoran; 3-diethylamino-6-ethoxyethyl-7-anilinofluoran; 3-diethylamino-7-methylfluoran; 3-diethylamino-7-chlorofluoran; 3-diethylamino-7-(m-trifluoromethylanilino)fluoran; 3-diethylamino-7-(o-chloroanilino)fluoran; 3-diethylamino-7-(p-chloroanilino)fluoran; 3-diethylamino-7-(o-fluoroanilino)fluoran; 3-diethylamino-benzo[a]fluoran;

3-diethylamino-benzo[c]fluoran; 3-dibutylamino-6-methyl-fluoran; 3-dibutylamino-6-methyl-7-anilinofluoran; 3-dibutylamino-6-methyl-7-(o,p-dimethylanilino)fluoran; 3-dibutylamino-6-methyl-7-(o-chloroanilino)fluoran; 3-dibutylamino-6-methyl-7-(p-chloroanilino)fluoran; 3-dibutylamino-6-methyl-7-(o-fluoroanilino)fluoran; 3-dibutylamino-6-methyl-7-(m-trifluoromethylanilino)fluoran; 3-dibutylamino-6-methyl-chlorofluoran; 3-dibutylamino-6-ethoxyethyl-7-anilinofluoran; 3-dibutylamino-6-chloro-7-anilinofluoran; 3-dibutylamino-6-methyl-7-p-methylanilinofluoran; 3-dibutylamino-7-(o-chloroanilino)fluoran; 3-dibutylamino-7-(O-fluoroanilino)fluoran; 3-di-pentylamino-6-methyl-7-anilinofluoran; 3-di-pentylamino-6-methyl-7-(p-chloroanilino)fluoran; 3-di-pentylamino-7-(m-trifluoromethylanilino)fluoran; 3-di-pentylamino-6-chloro-7-anilinofluoran; 3-di-pentylamino-7-(p-chloroanilino)fluoran; 3-pyrrolidino-6-methyl-7-anilinofluoran; 3-piperidino-6-methyl-7-anilinofluoran; 3-(N-methyl-N-propylamino)-6-methyl-7-anilinofluoran; 3-(N-methyl-N-cyclohexylamino)-6-methyl-7-anilinofluoran; 3-(N-ethyl-N-cyclohexylamino)-6-methyl-7-anilinofluoran; 3-(N-ethyl-N-xylylamino)-6-methyl-7-(p-chloroanilino)fluoran; 3-(N-ethyl-p-toluidino)-6-methyl-7-anilinofluoran; 3-(N-ethyl-N-isoamylamino)-6-methyl-7-anilinofluoran; 3-(N-ethyl-N-isoamylamino)-6-chloro-7-anilinofluoran; 3-(N-ethyl-N-tetrahydrofurfurylamino)-6-methyl-7-anilinofluoran; 3-(N-ethyl-N-isobutylamino)-6-methyl-7-anilinofluoran; 3-(N-ethyl-N-ethoxypropylamino)-6-methyl-7-anilinofluoran; 3-cyclohexylamino-6-chlorofluoran; 2-(4-oxahexyl)-3-dimethylamino-6-methyl-7-anilinofluoran; 2-(4-oxahexyl)-3-diethylamino-6-methyl-7-anilinofluoran; 2-(4-oxahexyl)-3-dipropylamino-6-methyl-7-anilinofluoran; 2-methyl-6-p-(p-dimethylaminophenyl)aminoanilinofluoran; 2-methoxy-6-p-(p-dimethylaminophenyl)aminoanilinofluoran; 2-chloro-3-methyl-6-p-(p-phenylaminophenyl)aminoanilinofluoran; 2-chloro-6-p-(p-dimethylaminophenyl)aminoanilinofluoran; 2-nitro-6-p-(p-diethylaminophenyl)aminoanilinofluoran; 2-amino-6-p-(p-diethylaminophenyl)aminoanilinofluoran; 2-diethylamino-6-p-(p-diethylaminophenyl)aminoanilinofluoran; 2-phenyl-6-methyl-6-p-(p-phenylaminophenyl)aminoanilinofluoran; 2-benzyl-6-p-(p-phenylaminophenyl)aminoanilinofluoran; 2-hydroxy-6-p-(p-phenylaminophenyl)aminoanilinofluoran; 3-methyl-6-p-(p-dimethylaminophenyl)aminoanilinofluoran; 3-diethylamino-6-p-(p-diethylaminophenyl)aminoanilinofluoran; 3-diethylamino-6-p-(p-dibutylaminophenyl)aminoanilinofluoran; 2,4-dimethyl-6-[(4-dimethylamino)anilino]fluoran <Fluorene Leuco Dye>

3,6,6'-tris(dimethylamino)spiro[fluorene-9,3'-phthalide], 3,6,6'-tris(diethylamino)spiro[fluorene-9,3'-phthalide].

<Divinyl Leuco Dye>

3,3-bis-[2-(p-dimethylaminophenyl)-2-(p-methoxyphenyl)ethenyl]-4,5,6,7-tetrabromophthalide; 3,3-bis-[2-(p-dimethylaminophenyl)-2-(p-methoxyphenyl)ethenyl]-4,5,6,7-tetrachlorophthalide; 3,3-bis-[1,1-bis(4-pyrrolidinophenyl)ethylen-2-yl]-4,5,6,7-tetrabromophthalide;

3,3-bis-[1-(4-methoxyphenyl)-1-(4-pyrrolidinophenyl)ethylen-2-yl]-4,5,6,7-tetrachlorophthalide.

<Other Leuco Dye>

3-(4-diethylamino-2-ethoxyphenyl)-3-(1-ethyl-2-methylindol-3-yl)-4-azaphthalide; 3-(4-diethylamino-2-ethoxyphenyl)-3-(1-octyl-2-methylindol-3-yl)-4-azaphthalide; 3-(4-cyclohexylethylamino-2-methoxyphenyl)-3-(1-ethyl-2-methylindol-3-yl)-4-azaphthalide; 3,3-bis(1-ethyl-2-methylindol-3-yl)phthalide; 3,6-bis(diethylamino)fluoran-γ-(3'-nitro)anilinolactam; 3,6-bis(diethylamino)fluoran-γ-(4'-nitro)anilinolactam; 1,1-bis[2',2',2",2"-tetrakis(p-dimethylaminophenyl)-ethenyl]-2,2-dinitrileethane; 1,1-bis[2',2',2",2"-tetrakis(p-dimethylaminophenyl)-ethenyl]-2-β-naphthoylethane; 1,1-bis[2',2',2",2"-tetrakis(p-dimethylaminophenyl)ethenyl]-2,2-diacetylethane; bis[2,2,2',2'-tetrakis(p-dimethylaminophenyl)ethenyl]-methylmalonic acid dimethyl ester.

<Sensitizer>

In the present invention, a known sensitizer may be used. While the sensitizer is not particularly limited, for example, 1,2-di(3-methylphenoxy)ethane, β-benzyloxynaphthalene, fatty acid amide having a carbon number of 10-21 (e.g., stearic acid amide, palmitic acid amide etc.), aromatic sulfonamide (e.g., benzenesulfonamide, m-toluenesulfonamide, o-toluenesulfonamide, p-toluenesulfonamide, 2-ethylbenzenesulfonamide, 3-ethylbenzenesulfonamide, 4-ethylbenzenesulfonamide, 2-propylbenzenesulfonamide, 3-propylbenzenesulfonamide, 4-propylbenzenesulfonamide, 2-isopropylbenzenesulfonamide, 3-isopropylbenzenesulfonamide, 4-isopropylbenzenesulfonamide, 2-chlorobenzenesulfonamide, 3-chlorobenzenesulfonamide, 4-chlorobenzenesulfonamide, 2-bromobenzenesulfonamide, 3-bromobenzenesulfonamide, 4-bromobenzenesulfonamide, 2-methoxybenzenesulfonamide, 3-methoxybenzenesulfonamide, 4-methoxybenzenesulfonamide, 2-ethoxybenzenesulfonamide, 3-ethoxybenzenesulfonamide, 4-ethoxybenzenesulfonamide, 2,3-dichlorobenzenesulfonamide, 3,4-dichlorobenzenesulfonamide, 2,5-dichlorobenzenesulfonamide, 4-bromo-2-methoxybenzenesulfonamide, 5-bromo-2-methoxybenzenesulfonamide etc.), ethylenebisamide, montanic acid wax, polyethylene wax, p-benzylbiphenyl, diphenylsulfone, 4-biphenyl-p-tolyl ether, m-terphenyl, 1,2-diphenoxyethane, dibenzyl oxalate, di(p-chlorobenzyl) oxalate, di(p-methylbenzyl) oxalate, dibenzyl terephthalate, benzyl p-benzyloxybenzoate, di-p-tolyl carbonate, phenyl-α-naphthyl carbonate, 1,4-diethoxynaphthalene, 1-hydroxy-2-naphthoic acid phenyl ester, o-xylene-bis(phenyl ether), 4-(m-methylphenoxymethyl)biphenyl, 4,4'-ethylenedioxy-bis-benzoic acid dibenzyl ester, dibenzoyloxymethane, 1,2-di(3-methylphenoxy)ethylene, bis[2-(4-methoxy-phenoxy) ethyl]ether, methyl p-nitrobenzoate, phenyl p-toluenesulfonate and the like can be used. Among these, 1,2-di(3-methylphenoxy)ethane, β-benzyloxynaphthalene, fatty acid amide having a carbon number of 10-21 (e.g., stearic acid amide, palmitic acid amide etc.), diphenylsulfone, and p-toluenesulfonamide are preferable, 1,2-di(3-methylphenoxy)ethane, diphenylsulfone and p-toluenesulfonamide are more preferable, and 1,2-di(3-methylphenoxy) ethane showing high color-developing sensitivity even with low energy is particularly preferable. Only one kind of these sensitizers may be used or two or more kinds thereof may be used in combination. Particularly, when 1,2-di(3-methylphenoxy)ethane and p-toluenesulfonamide or diphenylsulfone are use in combination, the resistance to plasticizer, and heat resistance are improved further. When a sensitizer is used, the amount thereof to be used is generally 0.1-10 parts by weight, preferably 0.5-8 parts by weight, particularly preferably 1-5 parts by weight, per 1 part by weight of the basic leuco dye.

<Stabilizer>

In the present invention, a stabilizer may be used to improve image stability of the thermal recording material. The stabilizer means one having an effect of improving image stability. Examples of the stabilizer include a hindered phenol compound, a UV absorber (e.g., benzophenone compound, triazole compound), an antioxidant and the like. Among these, a hindered phenol compound is preferable since it improves image stability of the recording part (heat resistance, moisture resistance, water resistance, resistance to plasticizer etc.) and reduces fading of the recording part (i.e., time-course achromatization due to long-term storage). The hindered phenol compound is explained below.

<Hindered Phenol Compound>

The hindered phenol compound has, in one molecule, generally not less than 1 and not more than 15, preferably not less than 2 and not more than 6, hydroxyphenyl groups. The hindered phenol compound generally has a molecular weight of not less than 200 and not more than 2000, preferably not less than 250 and not more than 1800, more preferably not less than 300 and not more than 1500. The melting point of the hindered phenol compound is preferably 100° C. or more and generally 300° C. or less.

Furthermore, a hindered phenol compound wherein, in at least one of the hydroxyphenyl groups contained in the hindered phenol compound, the carbon atom at the 2-position or the 6-position is bonded to a hydrogen atom (i.e., substituent is absent at the 2-position or the 6-position) when the position of the phenolic hydroxyl group is the 1-position, is preferable.

Examples of the hindered phenol compound include tris (hydroxyphenyl)alkane, a 1,1,3-tris-substituted butane compound and the like described in JP-B-S39-4469 or JP-A-S56-40629 and the like.

As the hindered phenol compound, a compound represented by the formula (2) can be mentioned.

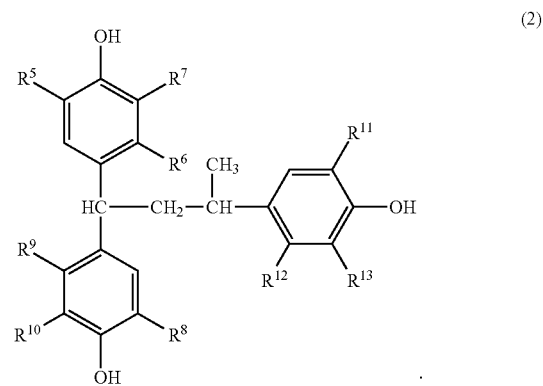

(2)

wherein $R^5$, $R^8$ and $R^{11}$ are each independently an alkyl group, and $R^6$, $R^7$, $R^9$, $R^{10}$, $R^{12}$ and $R^{13}$ are each independently a hydrogen atom or an alkyl group.

The alkyl group for $R^5$-$R^{13}$ may be linear, branched chain or cyclic. Specific examples of the alkyl group for $R^5$-$R^{13}$ include the specific examples of the alkyl group for $R^1$. The carbon number of the alkyl group for $R^5$-$R^{13}$ is preferably 1-8. The carbon number of the alkyl group for $R^5$, $R^8$ or $R^{11}$ is more preferably 1-6. The carbon number of the alkyl group for $R^6$, $R^7$, $R^9$, R, $R^{12}$ or $R^{13}$ is more preferably 1-5.

A combination wherein $R^6$, $R^7$, $R^9$, $R^{10}$, $R^{12}$ and $R^{13}$ are each independently a hydrogen atom or an alkyl group having a carbon number of 1-5 is preferable. Moreover, a combination wherein $R^6$, $R^9$ and $R^{12}$ are each a hydrogen atom or an alkyl group having a carbon number of 1-5, and at least one of $R^7$, $R^{10}$ and $R^{13}$ is a hydrogen atom is more preferable.

It is preferable that $R^5$, $R^8$ and $R^{11}$ be the same, or $R^6$, $R^9$ and $R^{12}$ be the same, or $R^7$, $R^{10}$ and $R^{13}$ be the same. It is more preferable that $R^5$, $R^8$ and $R^{11}$ be the same, $R^6$, $R^9$ and $R^{12}$ be the same, and $R^7$, $R^{10}$ and $R^{13}$ be the same. It is further more preferable that $R^5$, $R^8$ and $R^{11}$ be a tert-butyl group or a cyclohexyl group, $R^6$, $R^9$ and $R^{12}$ be a methyl group, and $R^7$, $R^{10}$ and $R^{13}$ be a hydrogen atom.

Examples of the compound (2) wherein $R^5$, $R^8$ and $R^{11}$ are tert-butyl groups, $R^6$, $R^9$ and $R^{12}$ are methyl groups, and $R^7$, $R^{10}$ and $R^{13}$ are hydrogen atoms include ADEKA STAB AO-30 (trade name) manufactured by ADEKA CORPORATION and OS-930 (trade name) manufactured by OSAKA SHINYAKU CO., LTD., which are commercially available. Examples of the compound (2) wherein $R^5$, $R^8$ and $R^{11}$ are cyclohexyl groups, $R^6$, $R^9$ and $R^{12}$ are methyl groups and $R^7$, $R^{10}$ and $R^{13}$ are hydrogen atoms include ADEKA ARKLS DH-43 (trade name) manufactured by ADEKA CORPORATION, which is commercially available. As compound (2), these commercially available products can be used particularly preferably.

As the hindered phenol compound, compounds represented by the formula (3)-the formula (9) can be mentioned.
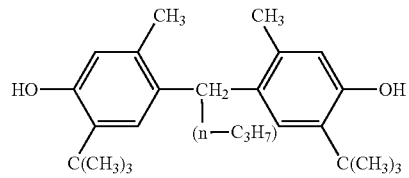
(3)
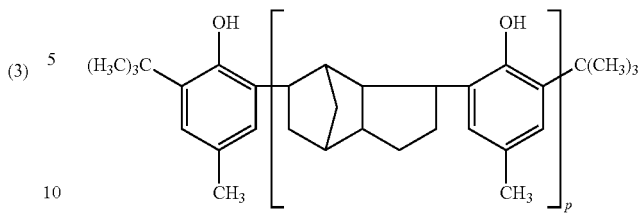
(4)
wherein p is 1 or 2.
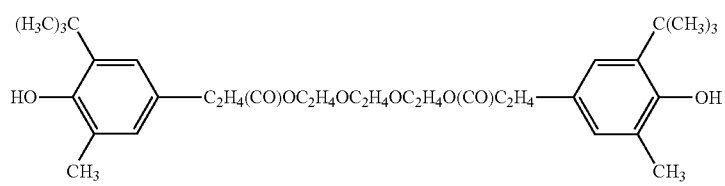
(5)
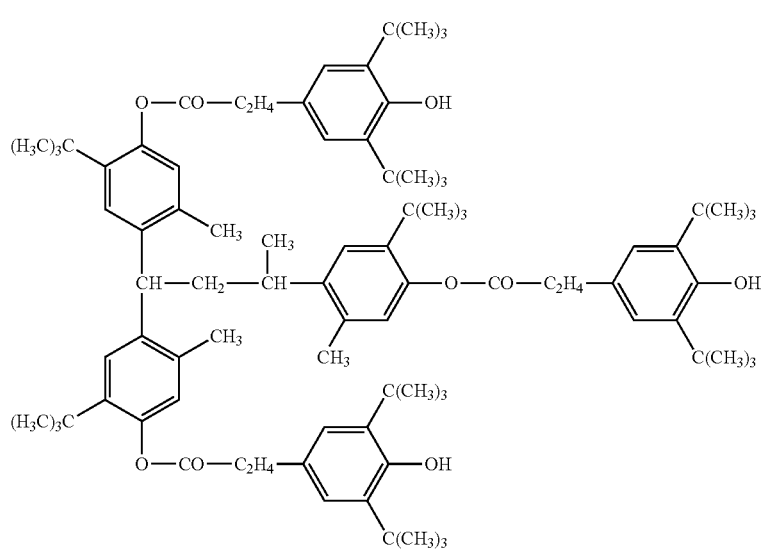
(6)
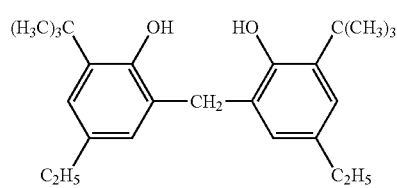
(7)
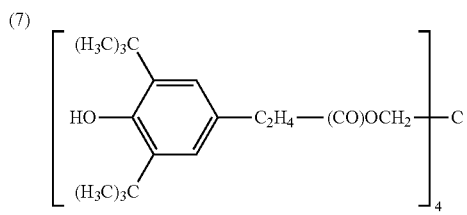
(8)
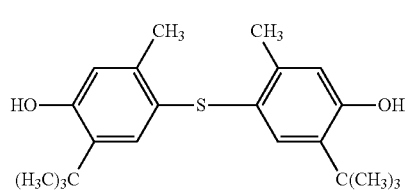
(9)

Among the aforementioned hindered phenol compounds, compound (2) (particularly, compound (2) wherein $R^5$, $R^9$ and are tert-butyl groups or cyclohexyl groups, $R^6$, $R^9$ and $R^{12}$ are methyl groups, and $R^7$, $R^{10}$ and $R^{13}$ are hydrogen atoms), compound (3) and compound (4) are preferable. Using compound (2)-compound (4), the background fog can be improved. Here, the improvement of background fog means suppression of unintended color development on the white area due to heating and the like.

Only one kind of a hindered phenol compound may be used or two or more kinds thereof may be used in combination. When a hindered phenol compound is used for the thermal recording material of the present invention, the content thereof is preferably 0.001-2 parts by weight, more preferably 0.005-1 part by weight, further preferably 0.01-0.5 parts by weight, per 1 part by weight of compound (1). When the content of the hindered phenol compound is less than such range, the moisture resistance, water resistance and heat resistance of the recording part may decrease, the recording part may fade due to the time-course changes, and suppression of color development on the white area due to heating may not be available. When it is more than such range, the color-developing sensitivity may decrease and the resistance of the recording part to plasticizers may decrease.

<Binder>

It is preferable to use a binder when forming a thermal recording layer. Examples of the binder include completely saponified polyvinyl alcohol, partially saponified polyvinyl alcohol, acetoacetylated polyvinyl alcohol, carboxy-modified polyvinyl alcohol, amide-modified polyvinyl alcohol, sulfonic acid-modified polyvinyl alcohol, butyral-modified polyvinyl alcohol, olefin-modified polyvinyl alcohol, nitrile-modified polyvinyl alcohol, pyrrolidone-modified polyvinyl alcohol, silicone-modified polyvinyl alcohol, other modified polyvinyl alcohols, hydroxyethyl cellulose, methyl cellulose, ethyl cellulose, carboxymethyl cellulose, polystyrene, styrene copolymers such as styrene-maleic anhydride copolymer, styrene-butadiene copolymer and the like, cellulose derivatives such as ethylcellulose and acetylcellulose and the like, casein, gum arabic, oxidized starch, etherified starch, dialdehyde starch, esterified starch, polyvinyl chloride, polyvinyl acetate, polyacrylamide, polyacrylic acid ester, polyvinyl butyral, polyamide resin, silicone resin, petroleum resin, terpene resin, ketone resin, cumarone resin and the like. The amount of the binder to be used is about 5-25 wt % of the solid content of the thermal recording layer.

The binder is generally used in the form of solution, emulsion, dispersion liquid, paste or a combination of these. Examples of the solvent in the solution, emulsion or dispersion liquid, or medium in the paste include water, alcohols, ketones, esters, hydrocarbons and the like.

<Crosslinking Agent>

Examples of the crosslinking agent include glyoxal, methylolmelamine, melamine formaldehyde resin, melamine urea resin, polyamine epichlorohydrin resin, polyamide epichlorohydrin resin, potassium persulfate, ammonium persulfate, sodium persulfate, ferric chloride, magnesium chloride, borax, boric acid, alum, ammonium chloride and the like. When a crosslinking agent is used, the amount thereof to be used is preferably 0.01-10 parts by weight per 1 part by weight of the basic leuco dye.

<Pigment>

Examples of the pigment include inorganic or organic pigments such as silica (excluding colloidal silica), calcium carbonate, kaolin, calcined kaolin, diatomite, talc, titanium oxide, aluminum hydroxide and the like. When a pigment is used, the amount thereof to be used is generally 0.1-20 parts by weight, preferably 0.5-10 parts by weight, per 1 part by weight of the basic leuco dye.

<Lubricant>

Examples of the lubricant include metal salt of fatty acid such as zinc stearate and calcium stearate, waxes, silicone resins and the like. When a lubricant is used, the amount thereof to be used is preferably 0.01-10 parts by weight per 1 part by weight of the basic leuco dye.

<Other Additive>

Examples of other additive include dispersing agent, antifoaming agent, fluorescence dye and the like. When other additive is used, the amount thereof to be used is preferably 0.01-10 parts by weight per 1 part by weight of the basic leuco dye.

<Support>

The support to be used in the thermal recording material of the present invention is not subject to any particular limitation with regard to its shape, structure, size, material and the like, and can be appropriately selected according to the object. Examples of the shape of the support include sheet, roll, flat plate and the like. The support may have a single layer structure or a laminate structure, and the size of the support can be appropriately selected according to the use of the object thermal recording material and the like. Examples of the material of the support include plastic film, synthetic paper, wood free paper, waste paper pulp, recycled paper, luster paper, oil proof paper, coated paper, art paper, cast coated paper, weak coated paper, resin laminated paper, release paper and the like. Alternatively, a composite sheet made of a combination thereof may be used as a support.

The thickness of the support is not particularly limited, and can be appropriately selected according to the object. It is preferably 30-2,000 μm, more preferably 50-1,000 μm.

<Protection Layer>

The thermal recording material of the present invention may have a protection layer on the thermal recording layer. In general, when a protection layer is formed on the thermal recording layer to improve the image stability of the thermal recording material, the color-developing sensitivity with low energy decreases. However, since compound (1) is used as a developer in the thermal recording material of the present invention, the color-developing sensitivity with low energy is fine even when a protection layer is formed on the thermal recording layer. The kind and amount of various components to be used for the protection layer are determined according to the requested property and recording suitability, and are not particularly limited.

<Under Layer, Back Layer, Intermediate Layer>

In the thermal recording material of the present invention, an under layer mainly composed of a pigment and a binder can also be formed between the support and the thermal recording layer, in an attempt to further increase the color-developing sensitivity. In addition, a back layer may be formed on the side opposite from the thermal recording layer of the support, in an attempt to remove curing of the thermal recording material. Furthermore, an intermediate layer may be formed between the support and the aforementioned under layer, between the thermal recording layer and the aforementioned protection layer, and between the support and the aforementioned back layer.

<Production Method of Thermal Recording Material>

The thermal recording material of the present invention can be produced by forming a thermal recording layer by applying a coating liquid containing a basic leuco dye and compound (1) and, where necessary, the second developer, a hindered phenol compound, a sensitizer and the like to at least one surface of the support and drying same. The coating liquid can be applied according to a well-known conventional technique. The application means is not particularly limited and, for example, an off-machine coater and an on-machine coater provided with various coaters such as air knife coater, rod blade coater, bent blade coater, beveled-blade coater, roll coater and curtain coater can be used.

The coating liquid for forming the thermal recording layer can be formed, for example, by finely pulverizing a basic leuco dye and compound (1), and, where necessary, the second developer, a hindered phenol compound, a sensitizer and the like in a grinding machine such as ball mill, attritor, sand grinder and the like or a suitable emulsifying apparatus to a particle size of several microns or below, and adding a binder and the like thereto. As the solvent for the coating liquid, water, alcohol and the like can be used. The solid content of the coating liquid is generally about 20-40 wt %.

The amount of the thermal recording layer to be coated can be appropriately determined according to its composition, use of the thermal recording material and the like. It is generally 1-20 g/m$^2$, preferably 2-12 g/m$^2$ in the dry weight.

In addition, the protection layer, under layer, back layer and intermediate layer can also be formed by applying a coating liquid containing the constituent components thereof in the same manner as with the aforementioned thermal recording layer and drying the coating liquid. Furthermore, the thermal recording material of the present invention after formation of each layer may also be subjected to a treatment known in the field (e.g., smoothing treatment by supercalender etc.).

EXAMPLES

The present invention is explained in detail in the following by referring to Examples, which are not to be construed as limitative.

Synthetic Example 1

Synthesis of Compound (a1)

4-Acetoxybenzenesulfonyl chloride (10 g), methyl salicylate (6.2 g) and toluene (50 g) were placed in a 100 ml four-necked flask, triethylamine (5.2 g) was added dropwise under stirring, and the mixture was reacted at room temperature for 3 hr. After completion of the reaction, the reaction mixture was neutralized with 2N hydrochloric acid, and the organic layer was washed several times with water. To the organic layer was added methanol (30 g), thionyl chloride (10 g) was added dropwise and the mixture was stirred at 30° C. for 1 hr and subjected to a deacetylation reaction. After completion of the reaction, the reaction mixture was neutralized with aqueous sodium hydrogen carbonate solution, the organic layer was washed several times with water, toluene was evaporated from the organic layer, and the obtained residue was purified by recrystallization method to give the object compound (a1) as white crystals.

As a result of the HPLC analysis, the purity of compound (a1) was 98 area %. The conditions of the analysis by high performance liquid chromatography (HPLC analysis) were as follows.
column: Inertsil ODS-2 manufactured by GL Sciences Inc.
particle size: 5 μm
inner diameter×length: inner diameter 4.6 mm×length 75 mm eluent: acetonitrile/0.05 vol % aqueous phosphoric acid solution=63/37
flow rate: 0.8 ml/min
wavelength: 220 nm
injection volume: 1 μL
column temperature: 40° C.
analysis time: 30 min
sample concentration: about 10 ppm The properties of the obtained compound (a1) were as is described below.
<Melting Point>
135° C. (measured according to JIS K 0064, hereinafter the same)
<IR Spectrum (ATR)>
3385 cm$^{-1}$ (νO—H), 1712 cm$^{-1}$ (νC═O), 1294, 1135 cm$^{-1}$ (νCO—O—)
<$^1$H-NMR spectrum (270 MHz, DMSO-d$_6$)>
10.9 ppm (1H, s), 7.78 ppm (1H, dd), 7.63 ppm (1H, ddd), 7.56 ppm (2H, d), 7.45 ppm (1H, ddd), 7.11 ppm (1H, dd), 6.94 ppm (2H, d), 3.72 ppm (3H, s)
<LC-MS (APCI/Negative)>
m/z=307 (M-H)$^-$ Synthetic Example 2

Synthesis of Compound (a2)

4-Acetoxybenzenesulfonyl chloride (10 g), ethyl salicylate (6.7 g) and toluene (50 g) were placed in a 100 mL four-necked flask, triethylamine (5.2 g) was added dropwise under stirring, and the mixture was reacted at room temperature for 3 hr. Thereafter, the treatments were performed according to Synthetic Example 1 to give the object compound (a2) as white crystals. As a result of HPLC analysis, the purity of compound (a2) was 98 area %. The properties of the obtained compound (a2) were as described below.
<Melting Point>
114° C.
<IR spectrum (ATR)>
3371 cm$^{-1}$ (νO—H), 1697 cm$^{-1}$ (νC═O), 1288, 1140 cm$^{-1}$ (νCO—O—)
<$^1$H-NMR spectrum (270 MHz, DMSO-d$_6$)>
10.9 ppm (1H, s), 7.77 ppm (1H, dd), 7.58 ppm (3H, m), 7.43 ppm (1H, ddd), 7.04 ppm (1H, dd), 6.93 ppm (2H, d), 4.18 ppm (2H, q), 1.26 ppm (3H, s)
<LC-MS (APCI/Negative)>
m/z=321 (M-H)$^-$ Synthetic Example 3

Synthesis of Compound (a3)

4-Acetoxybenzenesulfonyl chloride (10 g), propyl salicylate (7.3 g) and toluene (50 g) were placed in a 100 mL four-necked flask, triethylamine (5.2 g) was added dropwise under stirring, and the mixture was reacted at room temperature for 3 hr. Thereafter, the treatments were performed according to Synthetic Example 1 to give the object compound (a3) as white crystals. As a result of HPLC analysis, the purity of compound (a3) was 99 area %. The properties of the obtained compound (a3) were as described below.
<Melting Point>
121° C.
<IR spectrum (ATR)>
3347 cm$^{-1}$ (νO—H), 1699 cm$^{-1}$ (νC═O), 1283, 1169 cm$^{-1}$ (νCO—O—)
<$^1$H-NMR spectrum (270 MHz, DMSO-d$_5$)>
10.9 ppm (1H, s), 7.77 ppm (1H, dd), 7.59 ppm (3H, m), 7.44 ppm (1H, ddd), 7.06 ppm (1H, dd), 6.93 ppm (2H, d), 4.08 ppm (2H, t), 1.66 ppm (2H, sextet), 0.94 ppm (3H, t)
<LC-MS (APCI/Negative)>
m/z=335 (M-H)$^-$

Synthetic Example 4

Synthesis of Compound (a5)

4-Acetoxybenzenesulfonyl chloride (10 g), butyl salicylate (7.9 g) and toluene (50 g) were placed in a 100 mL four-necked flask, triethylamine (5.2 g) was added dropwise under stirring, and the mixture was reacted at room temperature for 3 hr. Thereafter, the treatments were performed according to Synthetic Example 1 to give the object compound (a5) as white crystals. As a result of HPLC analysis, the purity of compound (a5) was 99 area %. The properties of the obtained compound (a5) were as described below.

<Melting Point>
  110° C.
<IR spectrum (ATR)>
  3364 cm$^{-1}$ (vO—H), 1698 cm$^{-1}$ (vC=O), 1286, 1169 cm$^{-1}$ (vCO—O—)
<$^1$H-NMR spectrum (270 MHz, DMSO-d$_6$)>10.9 ppm (1H, s), 7.77 ppm (1H, dd), 7.62, 7.56 ppm (3H, m), 7.44 ppm (1H, td), 7.06 ppm (1H, dd), 6.94 ppm (2H, ddd), 4.12 ppm (2H, t), 1.62 ppm (2H, m), 1.39 ppm (2H, m), 0.92 ppm (3H, t)
<LC-MS (APCI/Negative)>
  m/z=349 (M-H)$^-$

Synthetic Example 5

Synthesis of Compound (a10)

4-Acetoxybenzenesulfonyl chloride (10 g), methyl p-hydroxybenzenecarboxylate (6.2 g) and toluene (50 g) were placed in a 100 mL four-necked flask, triethylamine (5.2 g) was added dropwise under stirring, and the mixture was reacted at room temperature for 3 hr. Thereafter, the treatments were performed according to Synthetic Example 1 to give the object compound (a10) as white crystals. As a result of HPLC analysis, the purity of compound (a10) was 99 area %. The properties of the obtained compound (a10) were as described below.

<Melting Point>
  131° C.
<IR spectrum (ATR)>
  3392 cm$^{-1}$ (vO—H), 1717 cm$^{-1}$ (vC=O), 1284, 1193 cm$^{-1}$ (vCO—O—)
<$^1$H-NMR spectrum (270 MHz, DMSO-d$_6$)>
  10.9 ppm (1H, s), 7.96 ppm (2H, d), 7.67 ppm (2H, d), 7.17 ppm (2H, d), 6.95 ppm (2H, d), 3.84 ppm (3H, s)
<LC-MS (APCI/Negative)>
  m/z=307 (M-H)$^-$ In the following Examples and Comparative Examples, an under layer and a thermal recording layer (heat-sensitive color developing layer) were formed on one surface of a support. In the following Examples and Comparative Examples, "parts" and "%" mean "parts by weight" and "wt %", respectively, unless particularly indicated. The smoothness of the thermal recording material was measured according to JIS P8119 (Beck method). A higher smoothness (seconds) means a more smooth surface.

<Under Layer Coating Liquid>
calcined kaolin (manufactured by BASF, trade name:

| | |
|---|---|
| ANSILEX 90) | 100.0 parts |
| styrene-butadiene copolymer latex (solid content 50%) | 30.0 parts |
| water | 170.0 parts |

A mixture of the above-mentioned composition was mixed with stirring to prepare an under layer coating liquid.

<Coating Liquid for Thermal Recording Layer>

The following liquids A-E were separately subjected to wet grinding by a sand grinder until the average particle size of each component in the liquid became 0.5 µm. The average particle size here is an average diameter in volume standard distribution, and was measured by a laser diffraction/scattering particle size distribution analyzer.

<Liquid A (Developer Dispersion)>

| | |
|---|---|
| (compound a1) | 6.0 parts |
| polyvinyl alcohol (10% aqueous solution) | 18.8 parts |
| water | 11.2 parts |

<Liquid B (Colorless Basic Leuco Dye Dispersion)>

| | |
|---|---|
| 3-dibutylamino-6-methyl-7-anilinofluorane (manufactured by YAMAMOTO CHEMICALS INC., trade name: ODB-2) | 2.0 parts |
| polyvinyl alcohol (10% aqueous solution) | 4.6 parts |
| water | 2.6 parts |

<Liquid C (Sensitizer Dispersion)>

| | |
|---|---|
| 1,2-di-(3-methylphenoxy)ethane (manufactured by SANKO CO., LTD., trade name: KS-232) | 6.0 parts |
| polyvinyl alcohol (10% aqueous solution) | 18.8 parts |
| water | 11.2 parts |

<Liquid D (Second Developer Dispersion)>

| | |
|---|---|
| bis(3-allyl-4-hydroxyphenyl)sulfone (manufactured by Nippon Kayaku Co., Ltd., trade name "TGSA"): | 6.0 parts |
| polyvinyl alcohol (10% aqueous solution): | 18.8 parts |
| water: | 11.2 parts |

<Liquid E (Hindered Phenol Compound Dispersion)>

| | |
|---|---|
| 1,1,3-tris(2-methyl-4-hydroxy-5-t-butylphenyl)butane (manufactured by OSAKA SHINYAKU CO., LTD., trade name: OS-930) | 6.0 parts |
| polyvinyl alcohol (10% aqueous solution) | 18.8 parts |
| water | 11.2 parts |

<Liquid F (Second Sensitizer Dispersion)>

| | |
|---|---|
| p-toluenesulfonamide: | 6.0 parts |
| polyvinyl alcohol (10% aqueous solution): | 18.8 parts |
| water: | 11.2 parts |

Example 1

Respective liquids were mixed at the following proportion to give coating liquid 1 for a thermal recording layer.

| | |
|---|---|
| liquid A (developer dispersion) | 36.0 parts |
| liquid B (colorless basic leuco dye dispersion) | 18.0 parts |
| Silica (manufactured by MIZUSAWA INDUSTRIAL CHEMICALS, LTD., trade name: P537 25% dispersion) | 40.0 parts |
| polyvinyl alcohol (10% aqueous solution) | 25.0 parts |

Then, a coating liquid for an under layer was applied with a meyer bar to one surface of wood free paper (substrate paper, 47 g/m$^2$), which is a support, such that the dry weight of the under layer was 10 g/m$^2$, and dried (fan dryer, 60° C., 2 min.) to form an under layer. Onto this under layer was applied the coating liquid 1 for the thermal recording layer such that the dry weight of the thermal recording layer was 3.5 g/m$^2$ and the liquid was dried (fan dryer, 60° C., 2 min), whereby the thermal recording layer was formed. A support having the under layer and the thermal recording layer was subjected to a treatment with a supercalender to achieve a smoothness of 500-1000 sec to give a thermal recording material.

Example 2

In the same manner as in Example 1 except that the compound (a1) in liquid A was changed to compound (a2), a thermal recording material was produced.

Example 3

In the same manner as in Example 1 except that the compound (a1) in liquid A was changed to compound (a3), a thermal recording material was produced.

Example 4

In the same manner as in Example 1 except that the compound (a1) in liquid A was changed to compound (a5), a thermal recording material was produced.

Example 5

In the same manner as in Example 1 except that the compound (a1) in liquid A was changed to compound (a10), a thermal recording material was produced.

Comparative Example 1

In the same manner as in Example 1 except that the compound (a1) in liquid A was changed to bisphenol A (i.e., 4,4'-isopropylidenediphenol), a thermal recording material was produced.

Comparative Example 2

In the same manner as in Example 1 except that the compound (a1) in liquid A was changed to 4-hydroxy-4'-isopropoxydiphenylsulfone, a thermal recording material was produced.

Comparative Example 3

In the same manner as in Example 1 except that the compound (a1) in liquid A was changed to bisphenol S (i.e., 4,4'-dihydroxydiphenylsulfone), a thermal recording material was produced.

Comparative Example 4

In the same manner as in Example 1 except that the compound (a1) in liquid A was changed to 4-hydroxy-4'-allyloxydiphenylsulfone, a thermal recording material was produced.

Comparative Example 5

In the same manner as in Example 1 except that the compound (a1) in liquid A was changed to 4'-methylphenyl 4-hydroxybenzenesulfonate, a thermal recording material was produced.

Comparative Example 6

In the same manner as in Example 1 except that the compound (a1) in liquid A was changed to 4'-tert-butylphenyl 4-hydroxybenzenesulfonate, a thermal recording material was produced.

Comparative Example 7

In the same manner as in Example 1 except that the compound (a1) in liquid A was changed to 4'-chlorophenyl 4-hydroxybenzenesulfonate, a thermal recording material was produced.

Example 6

Respective liquids were mixed at the following proportion to give coating liquid 2 for a thermal recording layer.

| | |
|---|---|
| liquid A (developer dispersion): | 36.0 parts |
| liquid B (colorless basic leuco dye dispersion): | 18.0 parts |
| liquid C (sensitizer dispersion): | 36.0 parts |
| Silica (manufactured by MIZUSAWA INDUSTRIAL CHEMICALS, LTD., trade name "P537", 25% dispersion): | 40.0 parts |
| polyvinyl alcohol (10% aqueous solution): | 25.0 parts |

Then, a coating liquid for an under layer was applied with a meyer bar to one surface of wood free paper (substrate paper, 47 g/m$^2$), which is a support, such that the dry weight of the under layer was 10 g/m$^2$, and dried (fan dryer, 60° C., 2 min.) to form an under layer. Onto this under layer was applied the coating liquid 2 for the thermal recording layer such that the dry weight of the thermal recording layer was 3.5 g/m$^2$ and the liquid was dried (fan dryer, 60° C., 2 min), whereby the thermal recording layer was formed. A support having the under layer and the thermal recording layer was subjected to a treatment with a supercalender to achieve a smoothness of 500-1000 sec to give a thermal recording material.

Example 7

In the same manner as in Example 6 except that 1,2-di(3-methylphenoxy)ethane in liquid C was changed to β-benzyloxynaphthalene, a thermal recording material was produced.

Example 8

In the same manner as in Example 6 except that 1,2-di(3-methylphenoxy)ethane in liquid C was changed to diphenylsulfone, a thermal recording material was produced.

Example 9

In the same manner as in Example 6 except that 1,2-di(3-methylphenoxy)ethane in liquid C was changed to stearic acid amide, a thermal recording material was produced.

Comparative Example 8

In the same manner as in Example 7 except that the compound (a1) in liquid A was changed to 4-hydroxy-4'-isopropoxydiphenylsulfone (manufactured by NIPPON SODA CO., LTD., trade name "D-8"), a thermal recording material was produced.

Comparative Example 9

In the same manner as in Example 8 except that the compound (a1) in liquid A was changed to 4-hydroxy-4'-isopropoxydiphenylsulfone (manufactured by NIPPON SODA CO., LTD., trade name "D-8"), a thermal recording material was produced.

Comparative Example 10

In the same manner as in Example 9 except that the compound (a1) in liquid A was changed to 4-hydroxy-4'-isopropoxydiphenylsulfone (manufactured by NIPPON SODA CO., LTD., trade name "D-8"), a thermal recording material was produced.

Comparative Example 11

In the same manner as in Example 6 except that the compound (a1) in liquid A was changed to 4-hydroxy-4'-allyloxydiphenylsulfone obtained by the method described in JP-B-2500532, a thermal recording material was produced.

Comparative Example 12

In the same manner as in Example 6 except that the compound (a1) in liquid A was changed to 4-hydroxy-4'-isopropoxydiphenylsulfone (manufactured by NIPPON SODA CO., LTD., trade name "D-8"), and 1,2-di(3-methylphenoxy) ethane in liquid C was changed to p-toluenesulfonamide, a thermal recording material was produced.

Example 10

Respective liquids were mixed at the following proportion to give coating liquid 3 for a thermal recording layer.

| | |
|---|---|
| liquid A (developer dispersion) | 25.2 parts |
| liquid B (colorless basic leuco dye dispersion) | 18.0 parts |
| liquid C (sensitizer dispersion) | 36.0 parts |
| liquid D (second developer dispersion) | 10.8 parts |
| silica (manufactured by MIZUSAWA INDUSTRIAL CHEMICALS, LTD., trade name: P537, 25% dispersion) | 40.0 parts |
| polyvinyl alcohol (10% aqueous solution) | 25.0 parts |

Then, a coating liquid for an under layer was applied with a meyer bar to one surface of wood free paper (substrate paper, 47 g/m$^2$), which is a support, such that the dry weight of the under layer was 10 g/m$^2$, and dried (fan dryer, 60° C., 2 min.) to form an under layer. Onto this under layer was applied the coating liquid 3 for the thermal recording layer such that the dry weight of the thermal recording layer was 3.5 g/m$^2$ and the liquid was dried (fan dryer, 60° C., 2 min), whereby the thermal recording layer was formed. A support having the under layer and the thermal recording layer was subjected to a treatment with a supercalender to achieve a smoothness of 500-1000 sec to give a thermal recording material.

Example 11

In the same manner as in Example 10 except that bis(3-allyl-4-hydroxyphenyl)sulfone in liquid D was changed to 4-hydroxy-4'-allyloxydiphenylsulfone obtained by the method described in JP-B-2500532, a thermal recording material was produced.

Example 12

In the same manner as in Example 10 except that bis(3-allyl-4-hydroxyphenyl)sulfone in liquid D was changed to 4-hydroxy-4'-propoxydiphenylsulfone (manufactured by API Corporation, trade name: TOMILAC KN), a thermal recording material was produced.

Example 13

In the same manner as in Example 10 except that bis(3-allyl-4-hydroxyphenyl)sulfone in liquid D was changed to bisphenol S (4,4'-dihydroxydiphenylsulfone), a thermal recording material was produced.

Example 14

In the same manner as in Example 10 except that bis(3-allyl-4-hydroxyphenyl)sulfone in liquid D was changed to bisphenol C (2,2'-bis(4-hydroxy-3-methylphenyl)propane), a thermal recording material was produced.

Example 15

In the same manner as in Example 10 except that bis(3-allyl-4-hydroxyphenyl)sulfone in liquid D was changed to bisphenol A (4,4'-isopropylidenediphenol), a thermal recording material was produced.

Example 16

In the same manner as in Example 10 except that bis(3-allyl-4-hydroxyphenyl)sulfone in liquid D was changed to the phenol-formalin condensation products described in WO02/098674 (manufactured by API Corporation, trade name: "TOMILAC 224"), a thermal recording material was produced.

Example 17

In the same manner as in Example 10 except that bis(3-allyl-4-hydroxyphenyl)sulfone in liquid D was changed to the diphenylsulfone compound described in JP-B-4004289 (manufactured by API Corporation, trade name: "TOMILAC 214"), a thermal recording material was produced.

Example 18

In the same manner as in Example 10 except that the amount of liquid A was changed to 36.0 parts, bis(3-allyl-4-hydroxyphenyl)sulfone in liquid D was changed to the diphenylsulfone compound described in JP-B-4004289 (manufactured by API Corporation, trade name: "TOMILAC 214"), a thermal recording material was produced.

Example 19

In the same manner as in Example 10 except that the amount of liquid A was changed to 32.4 parts, bis(3-allyl-4-hydroxyphenyl)sulfone in liquid D was changed to the diphenylsulfone compound described in JP-B-4004289 (manufactured by API Corporation, trade name: "TOMILAC 214"), and the amount of liquid D was changed to 3.6 parts, a thermal recording material was produced.

Example 20

In the same manner as in Example 10 except that bis(3-allyl-4-hydroxyphenyl)sulfone in liquid D was changed to the diphenylsulfone crosslinking type compound described in JP-B-3913820 (manufactured by Nippon Soda Co., Ltd., trade name: "D-90"), a thermal recording material was produced.

Example 21

In the same manner as in Example 10 except that the amount of liquid A was changed to 36.0 parts, and bis(3-allyl-4-hydroxyphenyl)sulfone in liquid D was changed to the diphenylsulfone crosslinking type compound described in JP-B-3913820 (manufactured by NIPPON SODA CO., LTD., trade name "D-90"), a thermal recording material was produced.

Example 22

In the same manner as in Example 10 except that the amount of liquid A was changed to 32.4 parts, bis(3-allyl-4-hydroxyphenyl)sulfone in liquid D was changed to the diphenylsulfone crosslinking type compound described in JP-B-3913820 (manufactured by NIPPON SODA CO., LTD., trade name "D-90"), and the amount of liquid D was changed to 3.6 parts, a thermal recording material was produced.

Example 23

In the same manner as in Example 10 except that the amount of liquid A was changed to 36.0 parts, and bis(3-allyl-4-hydroxyphenyl)sulfone in liquid D was changed to 4,4'-bis(3-(phenoxycarbonylamino)methylphenylureido)diphenylsulfone, a thermal recording material was produced.

Example 24

In the same manner as in Example 10 except that the amount of liquid A was changed to 36.0 parts, and bis(3-allyl-4-hydroxyphenyl)sulfone in liquid D was changed to N-(p-toluenesulfonyl)-N'-(3—p-toluenesulfonyloxyphenyl)urea described in JP-B-4601174, a thermal recording material was produced.

Example 25

Respective liquids were mixed at the following proportion to give coating liquid 4 for a thermal recording layer.

| | |
|---|---|
| liquid A (developer dispersion): | 36.0 parts |
| liquid B (colorless basic leuco dye dispersion): | 18.0 parts |
| liquid C (sensitizer dispersion): | 36.0 parts |
| liquid E (hindered phenol compound dispersion): | 3.6 parts |
| Silica (manufactured by MIZUSAWA INDUSTRIAL CHEMICALS, LTD., trade name "P537", 25% dispersion): | 40.0 parts |
| polyvinyl alcohol (10% aqueous solution): | 25.0 parts |

Then, a coating liquid for an under layer was applied with a meyer bar to one surface of wood free paper (substrate paper, 47 g/m²), which is a support, such that the dry weight of the under layer was 10 g/m², and dried (fan dryer, 60° C., 2 min.) to form an under layer. Onto this under layer was applied the coating liquid 4 for the thermal recording layer such that the dry weight of the thermal recording layer was 3.5 g/m² and the liquid was dried (fan dryer, 60° C., 2 min), whereby the thermal recording layer was formed. A support having the under layer and the thermal recording layer was subjected to a treatment with a supercalender to achieve a smoothness of 500-1000 sec to give a thermal recording material.

Example 26

In the same manner as in Example 25 except that 1,1,3-tris(2-methyl-4-hydroxy-5-t-butylphenyl)butane in liquid E was changed to 1,1,3-tris(2-methyl-4-hydroxy-5-cyclohexylphenyl)butane (manufactured by ADEKA CORPORATION, trade name: DH-43), a thermal recording material was produced.

Example 27

In the same manner as in Example 25 except that 1,1,3-tris(2-methyl-4-hydroxy-5-t-butylphenyl)butane in liquid E was changed to 4,4'-butylidenebis-(6-t-butyl-3-methylphenol) (manufactured by API Corporation, trade name: YOSHINOX BB), a thermal recording material was produced.

Example 28

In the same manner as in Example 25 except that 1,1,3-tris(2-methyl-4-hydroxy-5-t-butylphenyl)butane in liquid E was changed to oligomer type hindered phenol (manufactured by ELIOCHEM, trade name: WINGSTAY L), a thermal recording material was produced.

Example 29

In the same manner as in Example 25 except that the amount of liquid E was changed to 1.8 parts, a thermal recording material was produced.

Example 30

In the same manner as in Example 25 except that the amount of liquid A was changed to 35.64 parts, and the amount of liquid E was changed to 0.36 part, a thermal recording material was produced.

Example 31

In the same manner as in Example 25 except that the amount of liquid A was changed to 34.92 parts, and the amount of liquid E was changed to 1.08 parts, a thermal recording material was produced.

Example 32

In the same manner as in Example 25 except that the amount of liquid A was changed to 34.2 parts, and the amount of liquid E was changed to 1.8 parts, a thermal recording material was produced.

Example 33

In the same manner as in Example 25 except that the amount of liquid A was changed to 33.48 parts, and the amount of liquid E was changed to 2.52 parts, a thermal recording material was produced.

Example 34

Respective liquids were mixed at the following proportion to give coating liquid 5 for a thermal recording layer.

| | |
|---|---|
| liquid A (developer dispersion): | 36.0 parts |
| liquid B (colorless basic leuco dye dispersion): | 18.0 parts |
| liquid C (sensitizer dispersion): | 18.0 parts |
| liquid E (hindered phenol compound dispersion): | 1.8 parts |
| liquid F (second sensitizer dispersion): | 18.0 parts |
| Silica (manufactured by MIZUSAWA INDUSTRIAL CHEMICALS, LTD., trade name "P537", 25% dispersion): | 40.0 parts |
| polyvinyl alcohol (10% aqueous solution): | 25.0 parts |

Then, a coating liquid for an under layer was applied with a meyer bar to one surface of wood free paper (substrate paper, 47 g/m$^2$), which is a support, such that the dry weight of the under layer was 10 g/m$^2$, and dried (fan dryer, 60° C., 2 min.) to form an under layer. Onto this under layer was applied the coating liquid 5 for the thermal recording layer such that the dry weight of the thermal recording layer was 3.5 g/m$^2$ and the liquid was dried (fan dryer, 60° C., 2 min), whereby the thermal recording layer was formed. A support having the under layer and the thermal recording layer was subjected to a treatment with a supercalender to achieve a smoothness of 500-1000 sec to give a thermal recording material.

Example 35

In the same manner as in Example 34 except that 1,2-di(3-methylphenoxy)ethane in liquid C was changed to diphenylsulfone, a thermal recording material was produced.

Example 36

In the same manner as in Example 34 except that p-toluenesulfonamide in liquid F was changed to diphenylsulfone, a thermal recording material was produced.

The thermal recording materials obtained in the above-mentioned Examples and Comparative Examples were evaluated as follows.

<Color-Developing Sensitivity>

Using a thermal printer (TH-PMD) manufactured by OHKURA ELECTRIC CO., LTD, a gradation pattern was printed. The image concentration at application energy 0.26 mJ/dot and 0.35 mJ/dot and the density of the blank area were measured by a Macbeth densitometer (RD-914, using amber filter). The results are shown in Tables 1 and 3-5.

<Heat Resistance>

A thermal recording material was printed using a thermal printer (TH-PMD) manufactured by OHKURA ELECTRIC CO., LTD. at an application energy 0.35 mJ/dot to have a checkered pattern (one side of solid printed part, 0.8 cm) and left standing at 60° C. for 24 hr. The image concentration was measured by a Macbeth densitometer (RD-914, using amber filter). Table 2 shows image concentration, and image residual ratio calculated by the following formula, and Tables 6 and 7 show image residual ratio.

Image residual ratio(%)=100×(density of image after test)/(density of image before test)

<Background Fog>

A thermal recording material was printed using a thermal printer (TH-PMD) manufactured by OHKURA ELECTRIC CO., LTD. at an application energy 0.35 mJ/dot to have a checkered pattern (one side of solid printed part, 0.8 cm) and left standing at 60° C. for 24 hr. The concentration of the blank area was measured by a Macbeth densitometer (RD-914, using amber filter). The results are shown in Tables 2 and 8.

<Resistance to Plasticizer>

A thermal recording material was printed using a thermal printer (TH-PMD) manufactured by OHKURA ELECTRIC CO., LTD. at an application energy 0.35 mJ/dot to have a checkered pattern (one side of solid printed part, 0.8 cm), the front and back of the material were brought into contact with DIAWRAP manufactured by Mitsubishi Plastics, Inc. and the material was left standing at 23° C. for 2 hr. The image concentration and the concentration of the blank area were measured by a Macbeth densitometer (RD-914, using amber filter). Table 2 shows the blank area concentration, image concentration, and image residual ratio calculated by the following formula, and Tables 6 and 7 show image residual ratio.

Image residual ratio(%)=100×(image concentration after test)/(image concentration before test)

<Moisture Resistance>

A thermal recording material was printed using a thermal printer (TH-PMD) manufactured by OHKURA ELECTRIC CO., LTD. at an application energy 0.35 mJ/dot to have a checkered pattern (one side of solid printed part, 0.8 cm) and left standing for 24 hr in an environment of temperature 40° C., humidity 90%. The image concentration was measured by a Macbeth densitometer. Tables 6 and 7 show image residual ratio calculated by the following formula.

Image residual ratio(%)=100×(image concentration after test)/(image concentration before test)

<Water Resistance>

A thermal recording material was printed using a thermal printer (TH-PMD) manufactured by OHKURA ELECTRIC CO., LTD. at an application energy 0.35 mJ/dot to have a checkered pattern (one side of solid printed part, 0.8 cm), immersed in tap water at 20° C., and left standing for 24 hr. The image concentration was measured by a Macbeth densitometer. Tables 6 and 7 show image residual ratio calculated by the following formula.

Image residual ratio(%)=100×(image concentration after test)/(image concentration before test)

<Fading>

A thermal recording material was printed using a thermal printer (TH-PMD) manufactured by OHKURA ELECTRIC CO., LTD. at an application energy 0.26 mJ/dot and left standing at 20° C. for 1-2 months. The image concentration was measured by a Macbeth densitometer (RD-914, using amber filter). Table 9 shows image residual ratio calculated by the following formula.

Image residual ratio(%)=100×(image concentration after test)/(image concentration before test)

TABLE 1 color-developing sensitivity (no sensitizer)

| | | image concentration | |
|---|---|---|---|
| | blank area concentration | 0.26 mJ/dot | 0.35 mJ/dot |
| Ex. 1 | 0.06 | 0.85 | 1.29 |
| Ex. 2 | 0.07 | 0.87 | 1.26 |

TABLE 1-continued color-developing sensitivity (no sensitizer)

| | | image concentration | |
|---|---|---|---|
| | blank area concentration | 0.26 mJ/dot | 0.35 mJ/dot |
| Ex. 3 | 0.07 | 0.90 | 1.28 |
| Ex. 4 | 0.07 | 1.01 | 1.35 |
| Ex. 5 | 0.07 | 0.87 | 1.32 |
| Comp. Ex. 1 | 0.07 | 0.57 | 1.30 |
| Comp. Ex. 2 | 0.07 | 0.65 | 1.22 |
| Comp. Ex. 3 | 0.09 | 0.17 | 0.65 |
| Comp. Ex. 4 | 0.06 | 0.43 | 1.13 |

TABLE 2 background fog, heat resistance and resistance to plasticizer (no sensitizer)

| | before test | | background | heat resistance | | resistance to plasticizer | | |
|---|---|---|---|---|---|---|---|---|
| | blank area concentration | image concentration | fog blank area concentration | image concentration | image residual ratio (%) | blank area concentration | image concentration | image residual ratio (%) |
| Ex. 1 | 0.06 | 1.29 | 0.15 | 1.22 | 95 | 0.06 | 1.11 | 86 |
| Ex. 2 | 0.06 | 1.26 | 0.16 | 1.21 | 95 | 0.05 | 1.07 | 84 |
| Ex. 3 | 0.07 | 1.28 | 0.16 | 1.17 | 91 | 0.05 | 0.97 | 76 |
| Ex. 4 | 0.06 | 1.35 | 0.22 | 1.20 | 88 | 0.05 | 1.10 | 81 |
| Ex. 5 | 0.07 | 1.32 | 0.19 | 1.29 | 96 | 0.06 | 0.88 | 66 |
| Comp. Ex. 5 | 0.21 | 1.35 | 1.06 | 1.21 | 90 | 0.29 | 1.03 | 76 |
| Comp. Ex. 6 | 0.13 | 1.27 | 0.92 | 1.13 | 89 | 0.16 | 0.71 | 56 |
| Comp. Ex. 7 | 0.23 | 1.26 | 1.11 | 1.27 | 101 | 0.32 | 0.85 | 68 |

TABLE 3 color-developing sensitivity (with sensitizer)

| | | image concentration | |
|---|---|---|---|
| | blank area concentration | 0.26 mJ/dot | 0.35 mJ/dot |
| Ex. 6 | 0.06 | 1.28 | 1.38 |
| Ex. 7 | 0.06 | 1.21 | 1.28 |
| Ex. 8 | 0.06 | 1.17 | 1.32 |
| Ex. 9 | 0.06 | 1.08 | 1.32 |
| Ex. 10 | 0.08 | 1.32 | 1.42 |
| Ex. 11 | 0.06 | 1.30 | 1.39 |
| Ex. 12 | 0.07 | 1.27 | 1.37 |
| Ex. 13 | 0.08 | 1.28 | 1.39 |
| Ex. 14 | 0.07 | 1.29 | 1.34 |
| Ex. 15 | 0.07 | 1.29 | 1.36 |
| Ex. 16 | 0.06 | 1.27 | 1.34 |
| Ex. 17 | 0.06 | 1.24 | 1.31 |
| Ex. 18 | 0.07 | 1.27 | 1.35 |
| Ex. 19 | 0.07 | 1.29 | 1.36 |
| Ex. 20 | 0.06 | 1.23 | 1.32 |
| Ex. 21 | 0.07 | 1.28 | 1.36 |
| Ex. 22 | 0.06 | 1.30 | 1.34 |

TABLE 4 color-developing sensitivity (with sensitizer)

| | | image concentration | |
|---|---|---|---|
| | blank area concentration | 0.26 mJ/dot | 0.35 mJ/dot |
| Ex. 23 | 0.06 | 1.24 | 1.38 |
| Ex. 24 | 0.07 | 1.30 | 1.38 |
| Ex. 25 | 0.06 | 1.28 | 1.38 |
| Ex. 26 | 0.06 | 1.31 | 1.37 |
| Ex. 27 | 0.06 | 1.25 | 1.33 |
| Ex. 28 | 0.05 | 1.29 | 1.34 |
| Ex. 29 | 0.06 | 1.26 | 1.36 |
| Ex. 30 | 0.06 | 1.27 | 1.36 |

TABLE 4-continued color-developing sensitivity (with sensitizer)

| | | image concentration | |
|---|---|---|---|
| | blank area concentration | 0.26 mJ/dot | 0.35 mJ/dot |
| Ex. 31 | 0.06 | 1.26 | 1.35 |
| Ex. 32 | 0.06 | 1.26 | 1.35 |
| Ex. 33 | 0.06 | 1.26 | 1.34 |
| Ex. 34 | 0.06 | 1.20 | 1.35 |
| Ex. 35 | 0.06 | 1.18 | 1.38 |
| Ex. 36 | 0.06 | 1.27 | 1.37 |

TABLE 5 color-developing sensitivity (with sensitizer)

| | | image concentration | |
|---|---|---|---|
| | blank area concentration | 0.26 mJ/dot | 0.35 mJ/dot |
| Comp. Ex. 8 | 0.06 | 1.16 | 1.22 |
| Comp. Ex. 9 | 0.06 | 1.01 | 1.21 |
| Comp. Ex. 10 | 0.06 | 0.97 | 1.23 |
| Comp. Ex. 11 | 0.06 | 1.06 | 1.30 |
| Comp. Ex. 12 | 0.06 | 0.99 | 1.41 |

TABLE 6 heat resistance, resistance to plasticizer, moisture
resistance and water resistance (with sensitizer)

| | before test | | heat resistance image | resistance to plasticizer image | moisture resistance image | water resistance image |
|---|---|---|---|---|---|---|
| | blank area concentration | image concentration | residual ratio (%) | residual ratio (%) | residual ratio (%) | residual ratio (%) |
| Ex. 6 | 0.06 | 1.38 | 85 | 84 | 86 | 50 |
| Ex. 7 | 0.06 | 1.28 | 85 | 85 | 86 | 43 |
| Ex. 8 | 0.06 | 1.32 | 90 | 93 | 84 | 48 |
| Ex. 9 | 0.06 | 1.32 | 86 | 80 | 89 | 52 |
| Ex. 10 | 0.06 | 1.42 | 92 | 88 | 97 | 75 |
| Ex. 11 | 0.06 | 1.39 | 89 | 91 | 93 | 66 |
| Ex. 12 | 0.06 | 1.37 | 90 | 87 | 93 | 66 |
| Ex. 13 | 0.07 | 1.39 | 91 | 91 | 94 | 68 |
| Ex. 14 | 0.07 | 1.34 | 87 | 81 | 93 | 76 |
| Ex. 15 | 0.07 | 1.36 | 86 | 77 | 88 | 60 |
| Ex. 16 | 0.06 | 1.34 | 90 | 75 | 92 | 69 |
| Ex. 17 | 0.06 | 1.31 | 92 | 86 | 93 | 71 |
| Ex. 18 | 0.06 | 1.35 | 92 | 90 | 93 | 69 |
| Ex. 19 | 0.06 | 1.36 | 88 | 87 | 89 | 59 |
| Ex. 20 | 0.06 | 1.32 | 96 | 88 | 95 | 75 |
| Ex. 21 | 0.06 | 1.36 | 93 | 90 | 94 | 71 |
| Ex. 22 | 0.06 | 1.34 | 91 | 87 | 92 | 62 |

TABLE 7 heat resistance, resistance to plasticizer, moisture
resistance and water resistance (with sensitizer)

| | before test | | heat resistance image | resistance to plasticizer image | moisture resistance image | water resistance image |
|---|---|---|---|---|---|---|
| | blank area concentration | image concentration | residual ratio (%) | residual ratio (%) | residual ratio (%) | residual ratio (%) |
| Ex. 23 | 0.06 | 1.36 | 89 | 80 | 93 | 70 |
| Ex. 24 | 0.07 | 1.36 | 95 | 90 | 95 | 65 |
| Ex. 25 | 0.06 | 1.38 | 91 | 83 | 94 | 75 |
| Ex. 26 | 0.06 | 1.37 | 91 | 78 | 90 | 72 |
| Ex. 27 | 0.06 | 1.33 | 90 | 77 | 86 | 65 |
| Ex. 28 | 0.06 | 1.34 | 90 | 84 | 93 | 71 |
| Ex. 29 | 0.06 | 1.36 | 92 | 85 | 92 | 75 |
| Ex. 30 | 0.06 | 1.36 | 87 | 79 | 84 | 72 |
| Ex. 31 | 0.06 | 1.35 | 90 | 79 | 91 | 73 |
| Ex. 32 | 0.06 | 1.35 | 92 | 77 | 91 | 76 |
| Ex. 33 | 0.06 | 1.34 | 92 | 81 | 94 | 77 |
| Ex. 34 | 0.06 | 1.35 | 98 | 97 | 83 | 72 |
| Ex. 35 | 0.06 | 1.38 | 96 | 97 | 70 | 72 |
| Ex. 36 | 0.06 | 1.37 | 85 | 93 | 70 | 70 |

TABLE 8 background fog (with sensitizer)

| | before test | | background fog |
|---|---|---|---|
| | blank area concentration | image concentration | blank area concentration |
| Ex. 25 | 0.06 | 1.38 | 0.10 |
| Ex. 26 | 0.06 | 1.37 | 0.13 |
| Ex. 27 | 0.06 | 1.33 | 0.14 |
| Ex. 28 | 0.06 | 1.34 | 0.13 |
| Ex. 29 | 0.06 | 1.36 | 0.14 |
| Ex. 30 | 0.06 | 1.36 | 0.15 |
| Ex. 31 | 0.06 | 1.35 | 0.13 |
| Ex. 32 | 0.06 | 1.35 | 0.12 |
| Ex. 33 | 0.06 | 1.34 | 0.11 |
| Ex. 6 | 0.06 | 1.38 | 0.16 |

TABLE 9 fading (with sensitizer)

| | before test | | heat resistance | |
|---|---|---|---|---|
| | blank area concentration | image concentration | image concentration | image residual ratio (%) |
| Ex. 6 | 0.06 | 1.28 | 1.02 | 80 |
| Ex. 13 | 0.08 | 1.28 | 1.12 | 88 |
| Ex. 20 | 0.06 | 1.23 | 1.06 | 86 |
| Ex. 25 | 0.06 | 1.28 | 1.23 | 96 |
| Ex. 28 | 0.05 | 1.29 | 1.19 | 92 |
| Ex. 29 | 0.08 | 1.26 | 1.23 | 98 |
| Ex. 31 | 0.06 | 1.26 | 1.24 | 98 |
| Ex. 32 | 0.06 | 1.26 | 1.24 | 98 |

As is clear from the results in Table 1, Examples 1-5 using the compound (1) of the present invention as a developer showed high color-developing sensitivity with a low energy (application energy 0.26 mJ/dot) as compared to Comparative Examples 1-4 using conventional developers.

As is clear from the results in Table 2, Examples 1-5 using the compound (1) of the present invention as a developer showed good background fog and clear contrast between the blank area and the recorded area as compared to Comparative Examples 5-7 using an aryloxysulfonyl group-containing phenol derivative having an alkyl group or a chlorine atom instead of the —CO—OR$^1$ group (corresponding to the developer described in patent document 1). In addition, even after testing resistance to plasticizer, Examples 1-8 showed high image residual ratio and were superior in the durability to plasticizer as compared to Comparative Examples 5-7.

As is clear from the results of Tables 3-5, even with thermal recording materials using a sensitizer, Examples 6-36 using the compound (1) of the present invention as a developer showed high color-developing sensitivity with low energy (application energy 0.26 mJ/dot) as compared to Comparative Examples 8-12 using known developers.

As is clear from the results of Tables 6 and 7, even Examples 6-9 using a sensitizer in addition to the compound (1) of the present invention were superior in the resistance to plasticizer as compared to Comparative Examples 5-7. Moreover, Examples 10-24 using a second developer, Examples 25-33 using a hindered phenol compound, and Examples 34-36 using two kinds of sensitizers, in addition to the compound (1) of the present invention, were further superior in the heat resistance, moisture resistance and water resistance. Also, Examples 34-36 were particularly superior in the heat resistance and resistance to plasticizer.

As is clear from the results of Table 8, Examples 25-33 using a hindered phenol compound in addition to the compound (1) of the present invention were particularly superior in the background fog.

As is clear from the results of Table 9, Examples 13 and 20 using a second developer in addition to the compound (1) of the present invention were suppressed in the fading of the recorded area. Furthermore, Examples 25, 28, 29, 31 and 32 using a hindered phenol compound in addition to the compound (1) of the present invention were particularly superior in the suppression of fading of the recorded area.

As mentioned above, the compound (1) of the present invention is a developer superior in the balance of low energy color-developing sensitivity, background fog and image stability (heat resistance, resistance to plasticizer, moisture resistance, water resistance), and can provide a thermal recording material superior in the suppression of fading of the recorded area, and the like.

The invention claimed is:

1. A compound represented by formula (1)

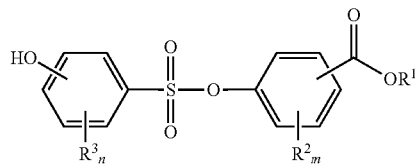
(1)

where:

R$^1$ is a hydrogen atom, an alkyl group, an alkenyl group, an aryl group or an aralkyl group, each R$^2$ is independently an alkyl group, an alkenyl group, an aryl group, an aralkyl group, an alkoxy group, a hydroxy group, a cyano group, a nitro group, a carboxy group or an amino group, each R$^3$ is independently an alkyl group, an alkenyl group, an aryl group, an aralkyl group, an alkoxy group, a hydroxy group, a cyano group, a nitro group, a carboxy group or an amino group, and m and n are each independently an integer of 0-4.

2. The compound according to claim 1, wherein the —CO—OR$^1$ group is bound to a carbon atom at the 2-position or 4-position of a benzene ring.

3. A developer, comprising the compound according to claim 1, wherein the developer is suitable for a thermal recording material.

4. A thermal recording material, comprising:

a support, and a thermal recording layer on the support, wherein the thermal recording layer comprises a colorless or pale-colored basic leuco dye and a developer for color development of the basic leuco dye, and the developer comprises the compound according to claim 1.

5. The thermal recording material according to claim 4, wherein the thermal recording layer comprises at least one sensitizer selected from the group consisting of 1,2-di-(3-methylphenoxy)ethane, fatty acid amide comprising from 10 to 21 carbon atoms, β-benzyloxynaphthalene, diphenylsulfone and p-toluenesulfonamide.

6. The thermal recording material according to claim 4, wherein the thermal recording layer comprises a hindered phenol compound.

7. The thermal recording material according to claim 6, wherein the hindered phenol compound is at least one selected from the group consisting of a compound represented by formula (2), a compound represented by formula (3) and a compound represented by formula (4):

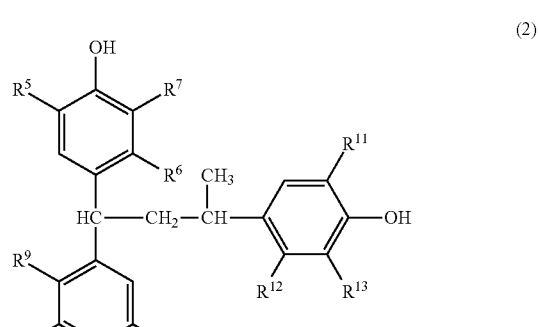
(2)

where R$^5$, R$^8$ and R$^{11}$ are each independently an alkyl group, and R$^6$, R$^7$, R$^9$, R$^{10}$, R$^{12}$ and R$^{13}$ are each independently a hydrogen atom or an alkyl group,

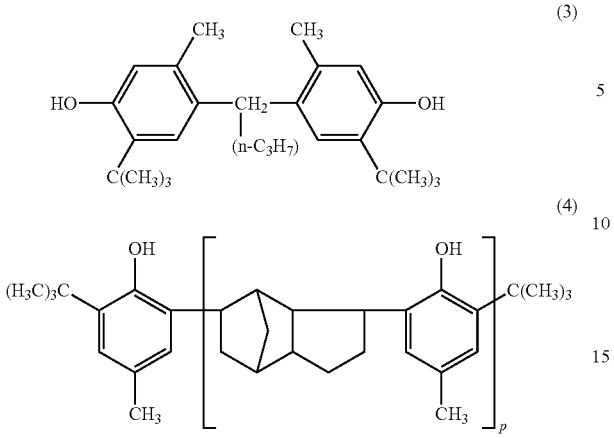

(3)

(4)

where p is 1 or 2.

8. The thermal recording material according to claim 7, wherein the hindered phenol compound is the compound represented by formula (2), where $R^5$, $R^8$ and $R^{11}$ are tert-butyl groups or cyclohexyl groups, $R^6$, $R^9$ and $R^{12}$ are methyl groups, and $R^7$, $R^{10}$ and $R^{13}$ are hydrogen atoms.

9. The thermal recording material according to claim 4, wherein the thermal recording layer comprises a second developer comprising a compound different from the compound according to claim 1.

10. The thermal recording material according to claim 9, wherein the second developer comprises at least one compound selected from the group consisting of a bisphenol sulfone compound, a bisphenol compound, a urea compound and a novolac type phenol compound.

11. The compound according to claim 1, wherein $R^1$ is an alkyl group comprising 1 to 8 carbon atoms.

12. The compound according to claim 1, wherein m is 0.

13. The compound according to claim 1, wherein n is 0.

14. The compound according to claim 1, wherein both m and n are 0.

15. The compound according to claim 1, wherein the position of the —CO—OR$^1$ group in the formula (1) is the 2-position relative to the carbon atom bonded to the oxy group in the benzene ring having the —CO—OR$^1$ group.

16. The compound according to claim 1, wherein the position of the —CO—OR$^1$ group in the formula (1) is the 4-position relative to the carbon atom bonded to the oxy group in the benzene ring having the —CO—OR$^1$ group.

17. The compound according to claim 1, wherein the position of the —OH group in the formula (1) is the 4-position relative to the carbon atom bonded to the sulfonyl group in the benzene ring having the —OH group.

18. The compound according to claim 1, having a formula selected from the group consisting of formulae (a1) to (a26):

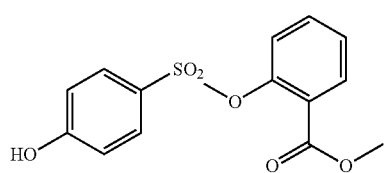
(a1)

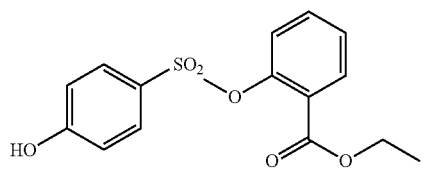
(a2)

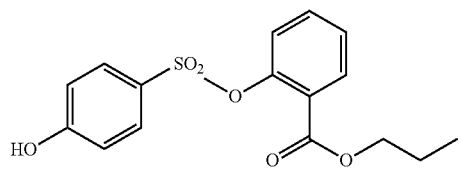
(a3)

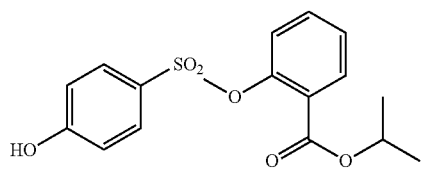
(a4)

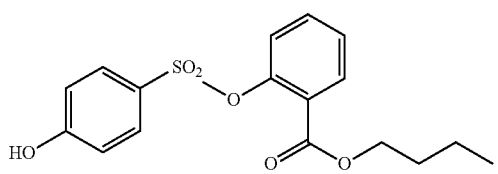
(a5)

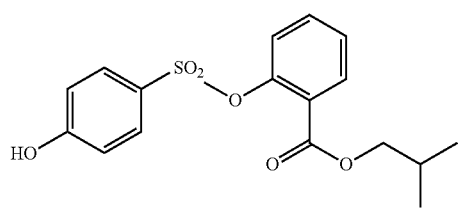
(a6)

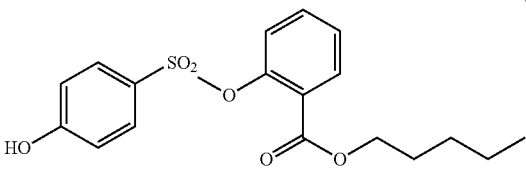
(a7)

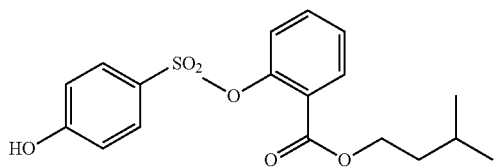
(a8)

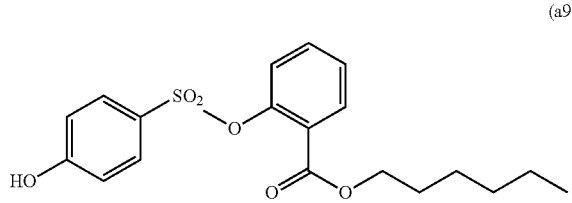
(a9)

(a10)
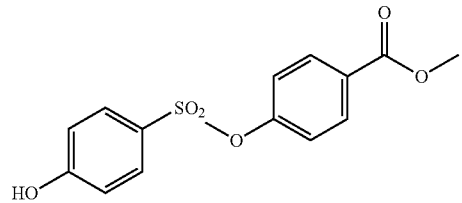
(a11)
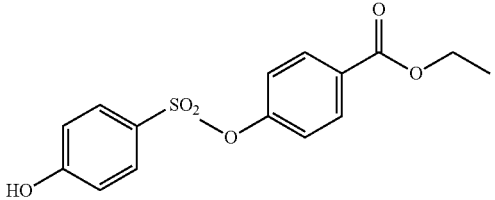
(a12)
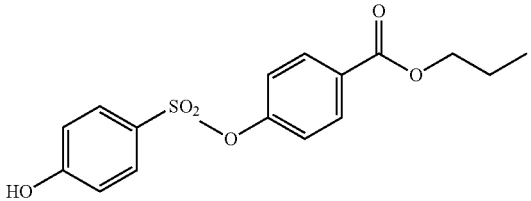
(a13)
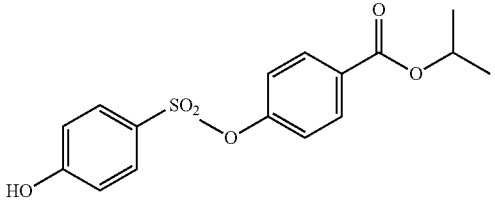
(a14)
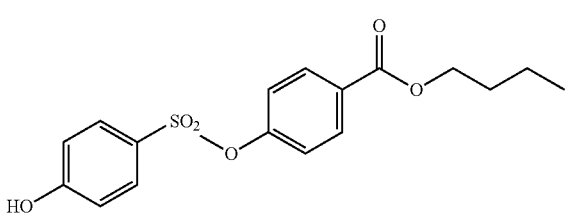
(a15)
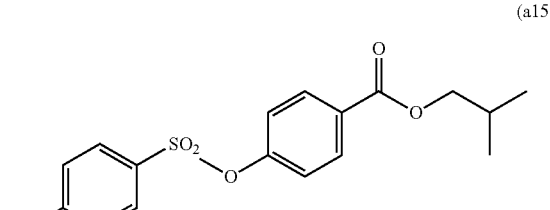
(a16)
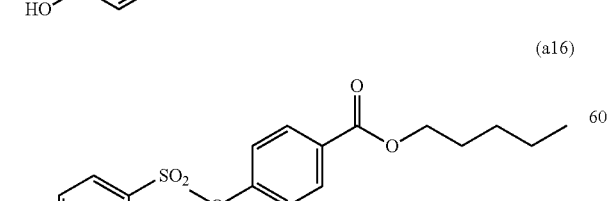
(a17)
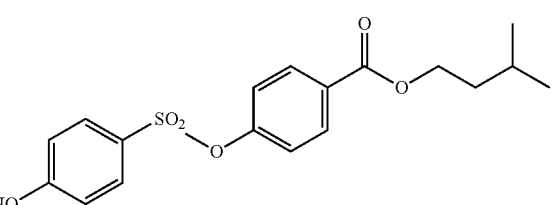
(a18)
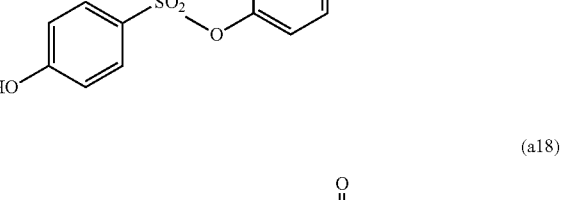
(a19)
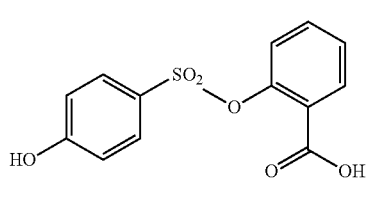
(a20)
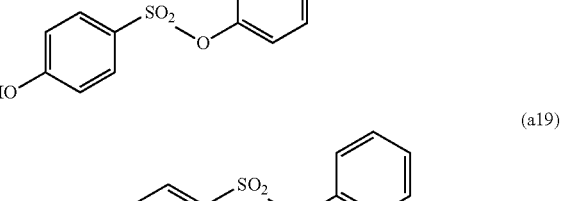
(a21)
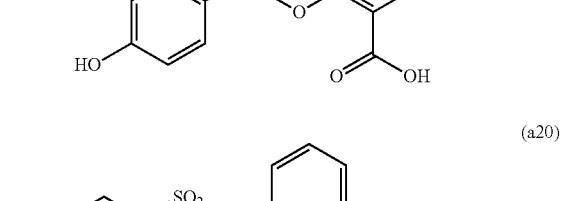
(a22)
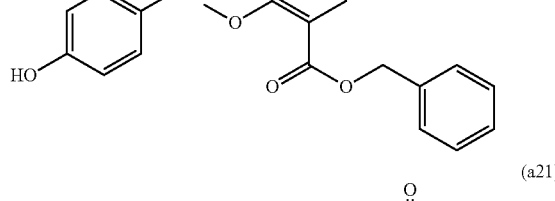
(a23)
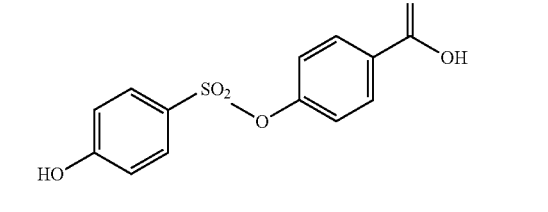

(a24)
(a25)
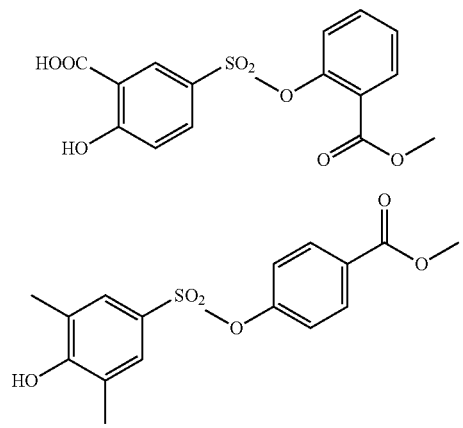
(a26)
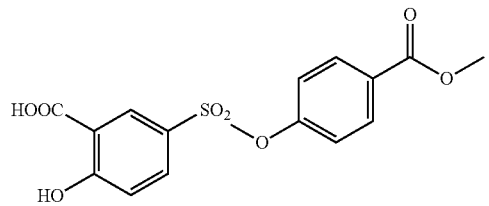
19. The compound according to claim 18, having a formula selected from the group consisting of formulae (a1), (a2), (a3), (a4), (a5) and (a10).
20. The compound according to claim 18, having a formula selected from the group consisting of formulae (a1), (a2), (a3) and (a5).
* * * * *